United States Patent [19]

Soyka et al.

[11] Patent Number: 5,286,736
[45] Date of Patent: Feb. 15, 1994

[54] PYRIDYL COMPOUNDS AND PHARMACEUTICAL COMPOSITIONS CONTAINING THESE COMPOUNDS

[75] Inventors: Rainer Soyka; Wolfgang Eisert; Thomas Mueller; Johannes Weisenberger, all of Biberach, Fed. Rep. of Germany

[73] Assignee: Dr. Karl Thomae GmbH, Biberach an der Riss, Fed. Rep. of Germany

[21] Appl. No.: 5,725

[22] Filed: Jan. 19, 1993

Related U.S. Application Data

[63] Continuation-in-part of Ser. No. 796,525, Nov. 22, 1991, abandoned.

Foreign Application Priority Data

Nov. 22, 1990 [DE] Fed. Rep. of Germany ....... 4037112

[51] Int. Cl.$^5$ ............................................. C07D 213/56
[52] U.S. Cl. .................................. 514/357; 514/336; 514/339; 546/273; 546/284; 546/331; 546/332; 546/335
[58] Field of Search ............... 546/273, 284, 331, 332, 546/335; 514/336, 339, 357

[56] References Cited

FOREIGN PATENT DOCUMENTS

| | | |
|---|---|---|
| 0111997 | 6/1984 | European Pat. Off. ............ 546/284 |
| 0287270 | 10/1988 | European Pat. Off. ............ 546/284 |
| 0397044 | 5/1990 | European Pat. Off. ............ 546/335 |

OTHER PUBLICATIONS

Chemical Abstracts, vol. 114, No. 21, Abstract 207035h, pp. 808–809, May 27, 1991.
Lefer, DN&P, 2(5), Aug. 1989, pp. 265–269.
Halushka, Kardiol, 78 (Suppl. 3) 1989, pp. 42–47.
O'Byrne et al, Eur. Respir. J., No. 2, 1989, pp. 782–786.
Smith, Eicosanoids, No. 2, 1989, pp. 199–212.

Primary Examiner—Alan L. Rotman
Assistant Examiner—Zinna N. Davis
Attorney, Agent, or Firm—David E. Frankhouser; Alan R. Stempel; Mary-Ellen Timbers

[57] ABSTRACT

New pyridyl derivatives of the formula

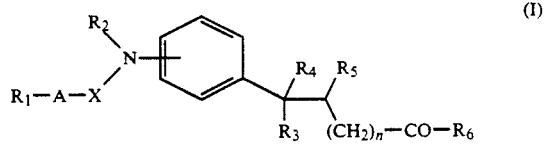

wherein
$R_1$ to $R_6$, A, X and n are as defined herein, the enantiomers thereof, the cis- and trans-isomers thereof if $R_4$ and $R_5$ together represent a carbon-carbon bond, and the addition salts thereof. The new pyridyl derivatives have antithrombotic activity and thromboxane-mediated activities. The new compounds are also simultaneously thromboxane antagonists (TRA) and thromboxane synthesis inhibitors (TSH). They also have an effect on PGE$_2$-production.

18 Claims, No Drawings

PYRIDYL COMPOUNDS AND PHARMACEUTICAL COMPOSITIONS CONTAINING THESE COMPOUNDS

This is a continuation-in-part of U.S. application Ser. No. 796,525, filed on Nov. 22. 1991 now abandoned.

This invention relates to new pyridyl derivatives of general formula

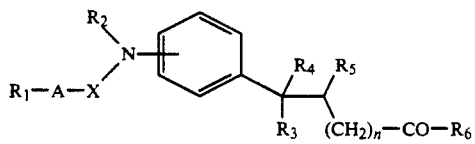

the enantiomers thereof, the cis- and trans-isomers thereof if $R_4$ and $R_5$ together represent a carbon-carbon bond, and the addition salts thereof, more particularly for pharmaceutical use the physiologically acceptable addition salts thereof with inorganic or organic bases if $R_6$ represents a hydroxy group, which have valuable pharmacological properties, especially antithrombotic effects. The new compounds are also thromboxane antagonists (TRA) and thromboxane synthesis inhibitors (TSH) and thus also inhibit the effects mediated by thromboxane. Moreover, they also have an effect on PGE-production in the lungs and on $PGD_2$-, $PGE_2$ and $PGF_2$ -production in human thrombocytes.

Thus, this invention relates to the new compounds of formula I above, the addition salts thereof with inorganic or organic bases, more particularly for pharmaceutical use the physiologically acceptable addition salts thereof, pharmaceutical compositions containing these compounds and processes for preparing them.

In the above general formula, n represents the number 2, 3 or 4,

X represents a carbonyl, thiocarbonyl or sulphonyl group, $R_1$ represents an optionally phenyl-substituted $C_{1-4}$-alkyl group, a $C_{5-7}$-cycloalkyl group, a phenyl group or, if A does not represent a bond, $R_1$ may also represent a benzoyl or benzenesulphonyl group in which the phenyl nucleus may in each case be mono-, di- or trisubstituted by fluorine, chlorine or bromine atoms or by $C_{1-4}$-alkoxy or $C_{1-4}$-alkyl groups, whilst the substituents may be identical or different and one of the substituents may also represent a trifluoromethyl, carboxyl, amino or nitro group, a naphthyl, biphenylyl, diphenylmethyl, indolyl, thienyl, chlorothienyl or bromothienyl group, $R_2$ represents a hydrogen atom or a $C_{1-4}$-alkyl group, $R_3$ represents a pyridyl group, $R_4$ and $R_5$ each represent a hydrogen atom or together represent another carbon-carbon bond, $R_6$ represents a hydroxy or $C_{1-3}$-alkoxy group and A represents a bond, a $C_{3-4}$-cycloalkylene or $C_{3-4}$-cycloalkylidene group wherein a methylene group may be replaced by a dichloromethylene group, a straight-chained, optionally mono- or polyunsaturated $C_{2-3}$-alkylene group, an —$R_7CR_8$—, —O—$R_7CR_8$— or —$NR_9$— group wherein $R_7$ represents a hydrogen atom, a hydroxy, phenyl or $C_{1-3}$-alkyl group, $R_8$ represents a hydrogen atom, a hydroxy, phenyl or $C_{1-3}$-alkyl group and $R_9$ represents a hydrogen atom or a $C_{1-3}$-alkyl group or a phenyl group.

As examples of the definitions of the groups mentioned hereinbefore, $R_1$ may represent, for example, a methyl, ethyl, n-propyl, isopropyl, n-butyl, tert.butyl, benzyl, 2-phenylethyl, 3-phenylpropyl, cyclobutyl, cyclopentyl, cyclohexyl, phenyl, benzoyl, benzenesulphonyl, fluorophenyl, fluorobenzoyl, fluorobenzenesulphonyl, chlorophenyl, chlorobenzoyl, chlorobenzenesulphonyl, bromophenyl, bromobenzoyl, bromobenzenesulphonyl, methylphenyl, methylbenzoyl, methylbenzenesulphonyl, ethylphenyl, ethylbenzoyl, ethylbenzenesulphonyl, n-propylphenyl, n-propylbenzoyl, n-propylbenzenesulphonyl, isopropylphenyl, isopropylbenzoyl, isopropylbenzene-sulphonyl, n-butylphenyl, n-butylbenzoyl, n-butylbenzenesulphonyl, isobutylphenyl, isobutylbenzoyl, isobutylbenzenesulphonyl, tert.butylphenyl, tert.butyl-benzoyl, tert.butylbenzenesulphonyl, trifluoromethyl-phenyl, trifluoromethylbenzoyl, trifluoromethylbenzene-sulphonyl, nitrophenyl, nitrobenzoyl, nitrobenzene-sulphonyl, aminophenyl, aminobenzoyl, aminobenzene-sulphonyl, carboxyphenyl, carboxybenzoyl, carboxybenzenesulphonyl, methoxyphenyl, methoxybenzoyl, methoxybenzenesulphonyl, ethoxyphenyl, ethoxybenzoyl, ethoxybenzenesulphonyl, isopropoxyphenyl, isopropoxy-benzoyl, isopropoxybenzenesulphonyl, difluorophenyl, difluorobenzoyl, difluorobenzenesulphonyl, dichloro-phenyl, dichlorobenzoyl, dichlorobenzenesulphonyl, dimethylphenyl, dimethylbenzoyl, dimethylbenzene-sulphonyl, dimethoxyphenyl, dimethoxybenzoyl, dimethoxybenzenesulphonyl, trimethylphenyl, trimethyl-benzoyl, trimethylbenzenesulphonyl, trimethoxyphenyl, trimethoxybenzoyl, trimethoxybenzenesulphonyl, chloro-methylphenyl, chloromethylbenzoyl, chloro-methylbenzenesulphonyl, chloro-methoxyphenyl, chloro-methoxybenzoyl, chloro-methoxybenzenesulphonyl, methoxymethylphenyl, methoxy-methylbenzoyl, methoxymethylbenzenesulphonyl, amino-dichlorophenyl, amino-dichlorobenzoyl, amino-dichlorobenzenesulphonyl, amino-dibromophenyl, amino-dibromobenzoyl, aminodibromobenzenesulphonyl, naphthyl, biphenyl, biphenylmethyl, indolyl, thienyl, chlorothienyl or bromothienyl group, $R_2$ may represent a hydrogen atom, a methyl, ethyl, n-propyl, isopropyl, n-butyl, isobutyl or tert.-butyl group, $R_3$ may represent a pyridyl-(2), pyridyl-(3) or pyridyl-(4) group, $R_6$ may represent a hydroxy, methoxy, ethoxy, n-propoxy or isopropoxy group and the —A—X— group may be a carbonyl, methylenecarbonyl, ethylenecarbonyl, n-propylenecarbonyl, ethenylene-carbonyl, ethynylenecarbonyl, sulphonyl, methylene-sulphonyl, gethylenesulphonyl, n-propylenesulphonyl, 1,1-cyclopropylenecarbonyl, 1,2-cyclopropylenecarbonyl, 3,3-dichloro-1,1-cyclopropylenecarbonyl, 3,3-dichloro-1,2cyclopropylenecarbonyl, 1,1-cyclobutylenecarbonyl, 1,2-cyclobutylenecarbonyl, carbonyl-1,2-cyclopropylene-carbonyl, carbonyl-1,2-cyclobutylene-carbonyl, oxymethylenecarbonyl, oxymethylmethylenecarbonyl, oxy-dimethylmethylenecarbonyl, oxy-n-ethylenecarbonyl, oxy-n-propylenecarbonyl, hydroxymethylenecarbonyl, aminocarbonyl, methylaminocarbonyl, ethylaminocarbonyl, n-propylaminocarbonyl, isopropylaminocarbonyl, n-butylaminocarbonyl, isobutylaminocarbonyl, phenylamino-carbonyl, aminothiocarbonyl, carbonylaminocarbonyl or sulphonylaminocarbonyl group, whilst the latter carbonyl or sulphonyl group is in each case connected to the —NR$_2$ group.

Preferred compounds of formula I above are, however, those wherein n represents the number 2, 3 or 4, X represents a carbonyl, thiocarbonyl or sulphonyl group, R$_1$ represents a phenyl group or, if A does not represent a bond, R$_1$ may also represent a benzoyl or benzenesulphonyl group, in which the phenyl nucleus may be monosubstituted in each case by a fluorine, chlorine or bromine atom, by a trifluoromethyl, phenyl, methoxy, carboxy or nitro group or by a C$_{1-4}$-alkyl group, or it may represent a phenyl group or, if A does not represent a bond, R$_1$ may also represent a benzoyl or benzenesulphonyl group in which the phenyl nucleus in each case is disubstituted by chlorine or bromine atoms or by methyl groups which substituents may be identical or different, or R$_1$ may represent a cyclohexyl, benzyl, 4-amino-3,5-dichlorophenyl, 4-amino-3,5-dibromophenyl, naphthyl, diphenylmethyl, indolyl, thienyl, chlorothienyl or bromothienyl group, R$_2$ represents a hydrogen atom or a C$_{1-3}$-alkyl group, R$_3$ represents a pyridyl group, R$_4$ and R$_5$ each represent a hydrogen atom or together represent another carbon-carbon bond, R$_6$ represents a hydroxy or C$_{1-3}$-alkoxy group and A represents a bond, a cyclopropylene or cyclopropylidene group wherein a methylene group may be replaced by a dichloromethylene group, a straight-chained, optionally mono- or polyunsaturated alkylene group having 2 carbon atoms, an —R$_7$CR$_8$-, —O—R$_7$CR$_8$- or —NR$_9$— group, wherein R$_7$ represents a hydrogen atom, a hydroxy or a C$_{1-2}$-alkyl group, R$_8$ represents a hydrogen atom or a C$_{1-2}$-alkyl group and R$_9$ represents a hydrogen atom, an alkyl group having 1 or 2 to 3 carbon atoms or a phenyl group, the enantiomers thereof, the cis- and trans-isomers thereof if R$_4$ and R$_5$ together represent a carbon-carbon bond, and the addition salts thereof with inorganic or organic bases.

However, the particularly preferred compounds are the compounds of formula I wherein n represents the numbers 2, 3 or 4, X represents a carbonyl, thiocarbonyl or sulphonyl group, R$_1$ represents a phenyl group optionally monosubstituted by a fluorine, chlorine or bromine atom, by a trifluoromethyl, phenyl, methoxy, carboxy or nitro group or by a C$_{1-4}$-alkyl group, or R$_1$ represents a phenyl group disubstituted by chlorine or bromine atoms or methyl groups the substituents being either identical or different, or a benzyl, 4-amino-3,5-dichlorophenyl, naphthyl or chlorothienyl group, R$_2$ represents a hydrogen atom or a methyl group, R$_3$ represents a 3-pyridyl group, R$_4$ and R$_5$ each represent a hydrogen atom or together represent another carbon-carbon bond, R$_6$ represents a hydroxy group and A represents a bond, a cyclopropylene or cyclopropylidene group, a straight-chained, optionally mono- or C$_2$-polyunsaturated alkylene group, an —R$_7$CR$_8$—, —O—R$_7$CR$_8$—, or —NR$_9$— group, wherein R$_7$ represents a hydrogen atom or a h.droxy or methyl group, R$_8$ represents a hydrogen atom or a methyl group and R$_9$ represents a hydrogen atom or a methyl or phenyl group, the enantiomers thereof, the cis- and trans-isomers thereof if R$_4$ and R$_5$ together form a carbon-carbon bond, and the physiologically acceptable addition salts thereof with inorganic or organic bases.

According to the invention, the new compounds are obtained by the following methods:

a) acylating a compound of general formula

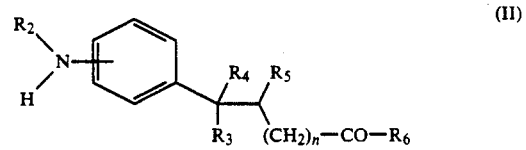

wherein

R$_2$ to R$_6$ and n are defined as hereinbefore, with a compound of general formula

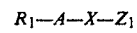   (III)

wherein

R$_1$ is defined as hereinbefore and

Z$_1$ represents a nucleophilic leaving group such as a halogen atom or an alkoxy group, e.g. a chlorine or bromine atom, a methoxy or ethoxy group or, if A represents an —NR$_9$— group and X represents a carbonyl or thiocarbonyl group, Z$_1$ together with R$_9$ represents another carbon-nitrogen bond.

The reaction is preferably carried out in a solvent such as methanol, ethanol, water/methanol, dioxane, tetrahydrofuran or chloroform, optionally in the presence of an acid binding agent such as potassium carbonate, triethylamine or pyridine, whilst these latter two may also be used as solvents, conveniently at temperatures between 0 and 50° C., but preferably at ambient temperature.

b) In order to prepare compounds of general formula I wherein R$_6$ represents a hydroxy group:

Cleaving a protecting group from a compound of general formula

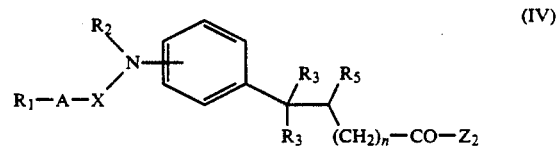

wherein

R$_1$ to R$_5$, A, X and n are defined as hereinbefore and

Z$_2$ represents a hydrolytically, thermolytically or hydrogenolytically removable protecting group for a carboxy group or a functional derivative of the carboxy group.

Examples of hydrolysable groups include functional derivatives of the carboxy group, such as the unsubstituted or substituted amides, esters, thioesters, orthoesters, iminoethers, amidines or anhydrides thereof, the nitrile group, ether groups such as the methoxy, ethoxy, tert.butoxy or benzyloxy group or lactones and examples of thermolytically removable groups include esters with tertiary alcohols, e.g. the tert.butylester, and examples of hydrogenolytically removable groups include aralkyl groups, e.g. the benzyl group.

The hydrolysis is expediently carried out either in the presence of an acid such as hydrochloric acid, sulphuric acid, phosphoric acid or trichloroacetic acid or in the presence of a base such as sodium hydroxide or potassium hydroxide in a suitable solvent such as water, water/methanol, ethanol, water/ethanol, water/isopropanol or water/dioxane at temperatures between $-10$ and $120°$ C., e.g. at temperatures between ambient temperature and the boiling temperature of the reaction mixture.

If, for example, a compound of formula IV contains a nitrile or aminocarbonyl group, these groups may preferably be converted into the carboxy group using 100% phosphoric acid at temperatures between 100 and 180° C., preferably at temperatures between 120 and 160° C., or with a nitrite, e.g. sodium nitrite, in the presence of an acid such as sulphuric acid, whilst the latter may conveniently be used as solvent at the same time, at temperatures between 0 and 50° C.

If, for example, a compound of formula IV contains an acid amide group such as the diethylaminocarbonyl or piperidinocarbonyl group, this group may preferably be converted such as hydrochloric acid, sulphuric acid, phosphoric acid or trichloroacetic acid or in the presence of a base such as sodium hydroxide or potassium hydroxide in a suitable solvent such as water, water/methanol, ethanol, water/ethanol, water/isopropanol or water/dioxane at temperatures between $-10$ and $120°$ C., e.g. at temperatures between ambient temperature and the boiling temperature of the reaction mixture.

If, for example, a compound of formula IV contains the tert.butyloxycarbonyl group, the tert.butyl group may also be thermally cleaved, optionally in an inert solvent such as methylene chloride, chloroform, benzene, toluene, tetrahydrofuran or dioxane and preferably in the presence of a catalytic quantity of an acid such as p-toluenesulphonic acid, sulphuric acid, phosphoric acid or polyphosphoric acid, preferably at the boiling temperature of the solvent used, e.g. at temperatures between 40 and 100° C.

If, for example, a compound of formula IV contains the benzyloxy or benzyloxycarbonyl group, the benzyl group may also be hydrogenolytically cleaved in the presence of a hydrogenation catalyst such as palladium/charcoal in a suitable solvent such as methanol, ethanol, methanol/water, ethanol/water, glacial acetic acid, ethyl acetate, dioxane or dimethylformamide, preferably at temperatures between 0 and 50° C., e.g. at ambient temperature and under a hydrogen pressure of from 1 to 5 bar. During hydrogenolysis, a halogen-containing compound may be dehalogenated at the same time and any double bond present may be hydrogenated.

c) In order to prepare compounds of general formula I wherein $R_4$ and $R_5$ each represent a hydrogen atom:

Hydrogenation of a compound of general formula

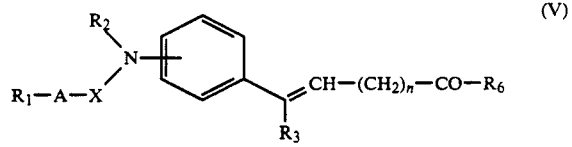

wherein $R_1$ to $R_3$, $R_6$, A, X and n are defined as hereinbefore.

The hydrogenation is carried out in a suitable solvent such as methanol, ethanol, dioxane, ethyl acetate or glacial acetic acid with catalytically activated hydrogen, e.g. with hydrogen in the presence of a hydrogenation catalyst such as Raney nickel, palladium, palladium/charcoal, platinum or platinum/charcoal and under a hydrogen pressure of from 1 to 5 bar, or with nascent hydrogen, e.g. in the presence of iron/hydrochloric acid, zinc/glacial acetic acid, tin(II)chloride/hydrochloric acid or iron(II)-sulphate/sulphuric acid, at temperatures between 0 and 50° C., preferably at ambient temperature. However, the catalytic hydrogenation may also be carried out stereo-selectively in the presence of a suitable catalyst.

Any nitro group optionally present in the group $R_1$ may be reduced at the same time and any chlorine or bromine atom optionally present in the group $R_1$ may be replaced by a hydrogen atom.

d) In order to prepare compounds of general formula I wherein $R_4$ and $R_5$ together represent a carbon-carbon bond:

Reaction of a compound of general formula

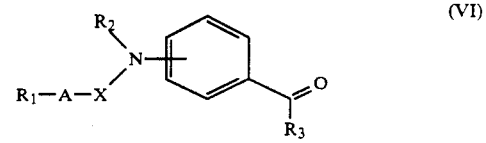

wherein $R_1$ to $R_3$, A and X are defined as hereinbefore, with a compound of general formula

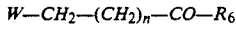

$$W-CH_2-(CH_2)_n-CO-R_6 \quad \text{(VII)}$$

wherein $R_6$ and n are defined as hereinbefore and

W represents a triphenylphosphonium halide, dialkylphosphonic acid or magnesium halide group, optionally with subsequent dehydration.

The reaction is preferably carried out in a suitable solvent such as diethylether, tetrahydrofuran, dioxane or dimethylformamide at temperatures between $-30$ and $100°$ C., preferably at temperatures between $-20$ and $25°$ C.

However, the reaction with a triphenylphosphonium halide of formula VII is carried out particularly advantageously in the presence of a base such as potassium tert.butoxide or sodium hydride.

If, during the reaction with a magnesium halide of formula VII, in the carbinol which is formed initially in the reaction mixture, the hydroxy group is not cleaved during the reaction, it will be cleaved in the presence of an acid such as hydrochloric acid, sulphuric acid, phosphoric acid or trichloroacetic acid or in the presence of a base such as sodium hydroxide or potassium hydroxide in a suitable solvent such as ethanol, isopropanol or dioxane at temperatures between 0 and 120° C., e.g. at temperatures between ambient temperature and the boiling temperature of the reaction mixture.

If, according to the invention, a compound of formula I is obtained wherein $R_2$ represents a hydrogen atom, this may be converted by alkylation into a corresponding compound of formula I wherein $R_2$ represents an alkyl group, or if a compound of formula I is obtained wherein $R_6$ represents a hydroxy group, this may be converted by esterification into a corresponding compound of formula I wherein $R_6$ represents an alkoxy group.

The subsequent alkylation is preferably carried out in a solvent such as methylene chloride, tetra-hydrofuran, dimethylformamide or dimethylsulphoxide in the presence of an alkylating agent such as methyliodide, dimethylsulphate, ethyl bromide, n-propylbromide or isopropylbromide, optionally in the presence of an acid-binding agent such as potassium carbonate at temperatures between 0 and 70° C., preferably at temperatures between 20 and 50° C.

The subsequent esterification or amidation is conveniently carried out in a solvent, e.g. in an excess of the alcohol used, such as methanol, ethanol or isopropanol, or an excess of the amine used, such as ammonia, methylamine, n-propylamine or dimethylamine, in the presence of an acid-activating agent such as thionyl chloride or hydrogen chloride gas at temperatures between 0 and 180° C., but preferably at the boiling temperature of the reaction mixture.

The compounds of formula I obtained may also be resolved into their enantiomers. Thus, the compounds of formula I obtained which contain only one optically active centre may be resolved into their optical antipodes using methods known per se (see Allinger N. L. and Eliel W. L. in "Topics in Stereochemistry", Vol. 6, Wiley Interscience, 1971), e.g. by recrystallisation from an optically active solvent or by reaction with an optically active substance which forms salts with the racemic compound, more particularly a base, and separating the salt mixture thus obtained, e.g. by using their different solubilities, into the diastereomeric salts from which the free antipodes can be liberated by the action of suitable agents. The D- and L-forms of α-phenyl-ethylamine or cinchonidine are examples of particularly useful optically active bases.

Furthermore, the compounds of formula I obtained having at least 2 asymmetric carbon atoms can be resolved into their diastereomers on the basis of their physical-chemical differences using methods known per se, e.g. by chromatography and/or fractional crystallisation. A pair of enantiomers thus obtained can subsequently be resolved into the optical antipodes thereof, as described above. If, for example, a compound of formula I contains two optically active carbon atoms, the corresponding (R R', S S')- and (R S', S R')-forms are obtained.

In addition, the compounds of formula I thus obtained wherein $R_4$ and $R_5$ together represent a carbon-carbon bond, may be converted into their cis- and trans-isomers by conventional methods, e.g. by chromatography on a carrier such as silica gel or by crystallisation.

Furthermore, the new compounds of formula I thus obtained, should they contain a carboxy group, may, if desired, be converted subsequently into the addition salts thereof with inorganic or organic bases, more particularly, for pharmaceutical use, into the physiologically acceptable addition salts thereof. Examples of bases include sodium hydroxide, potassium hydroxide, cyclohexylamine, ethanolamine, diethanolamine and triethanolamine.

The compounds of formulae II to VII used as starting materials may be obtained by methods known from the literature or are themselves known from the literature.

A compound of formula II used as starting material is obtained from a corresponding N-acylamino compound by Friedel-Craft acylation, subsequent deacylation, optionally followed by reduction, hydrolysis and/or esterification or by reacting a corresponding magnesium or lithium compound with a suitably substituted pyridine compound such as 3-cyano-pyridine, pyridine-3-aldehyde or a pyridine-3-carboxylic acid derivative, optionally followed by oxidation.

The compounds of formulae IV, V and VI used as starting materials are obtained by reacting a corresponding amino compound with a corresponding halide.

The compounds of formula VII used as starting materials are obtained by reacting a corresponding halocarboxylic acid with triphenylphosphine or with a trialkylphosphoester.

As already mentioned hereinbefore, the new compounds and the physiologically acceptable addition salts thereof with inorganic or organic bases have valuable pharmacological properties, particularly antithrombotic effects and an inhibitory effect on platelet aggregation. They are also thromboxane antagonists and thromboxane synthesis inhibitors, and it is particularly notable that the compounds of formula I have these effects simultaneously. They also have an effect on $PGE_2$-production in the lungs and on $PGD_2$-, $PGE_2$- and $PGF_2$-production in human thrombocytes.

By way of example, the following compounds:

| | |
|---|---|
| A = | (−)-5E-6-[4-(Z-2-(4-chlorophenyl)-cyclopropyl-1-carboxamido)-phenyl]-6-(3-pyridyl)-hex-5-enoic acid, |
| B = | 5E-6-[3-(3-(4-chlorophenyl)-propionylamino)-phenyl]-6-(3-pyridyl)-hex-5-enoic acid, |
| C = | 5E-6-[3-(3-(4-chlorophenyl)-thioureido)-phenyl]-6-(3-pyridyl)-hex-5-enoic acid, and |
| D = | 5E-6-[3-(3-(2,4-dichlorophenyl)-1-methylthioureido)-phenyl]-6-(3-pyridyl)-hex-5-enoic acid | were tested for their biological properties as follows:

1. Antithrombotic activity

Method

The thrombocyte aggregation is measured using the Born and Cross method (J. Physiol. 170: 397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of the aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used. Before the addition of the collagen the plasma is incubated for 10 minutes with the substance at 37° C.

From the measurements obtained an $EC_{50}$ is determined graphically, indicating a 50% change in the optical density in terms of the inhibition of aggregation.

2. Thromboxane-antagonistic activity

Venous human blood is anti-coagulated with 13 mM $Na_3$ citrate and centrifuged for 10 minutes at 170×g. The supernatant platelet-rich plasma is passed through a Sepharose 2B column in order to remove the plasma proteins. Aliquots of the platelet suspension obtained are incubated with the test substance, the ligand ($^3$H-labelled) and a marker ($^{14}$C-labelled) for 60 minutes at ambient temperature and then centrifuged for 20 seconds at 10,000×g. The supernatant is removed and the pellet is dissolved in NaOH. The $^3$H activity in the supernatant corresponds to the free ligand, $^{14}$C gives the concentration of the marker. $^3$H in the pellet corresponds to the bound ligand whilst $^{14}$C is used to correct for the ligand in the extracellular space. After the process has been repeated, the displacement curve is determined from the binding values for different concentrations of the test substance and the $IC_{50}$ is determined.

3. Determining the inhibitory effect on thromboxane synthetase

Venous human blood is anti-cogulated with 13 mM $Na_3$ citrate and centrifuged for 10 minutes at 170×g. The supernatant platelet-rich plasma is passed through a Sepharose 2B column in order to remove the plasma proteins. Aliquots of the platelet suspension obtained are incubated with the test substance or with a solvent as control for 10 minutes at ambient temperature and after the addition of $^{14}$C-labelled arachidonic acid incubation is continued for a further 10 minutes. After this has been stopped with 50μl of citric acid, extraction is carried out 3× with 500μl of ethyl acetate and the combined extracts are distilled off with nitrogen. The residue is taken up in ethyl acetate, placed on TLC film and separated with chloro-form:methanol:glacial acetic acid:water (90:8:1:0.8, v/v/v/v). The dried TLC films are placed on X-ray film for 3 days, the autoradiograms are developed and the active zones are marked on the film using the autoradiograms. After cutting out, the activity is measured in a scintillation counter and the inhibition of the formation of TXB2 is calculated. The $IC_{50}$ is determined by linear interpolation.

The Table which follows contains the values found:

| Example | Inhibition of thromboxane synthetase $IC_{50}$ | Thromboxane-antagonistic activity $IC_{50}$ | Inhibition of collagen-induced aggregation $EC_{50}$ |
| --- | --- | --- | --- |
| A | 0.004 μM/l | 0.004 μM/l | 0.5 μM/l |
| B | 0.004 μM/l | 0.008 μM/l | 2.2 μM/l |
| C | 0.032 μM/l | 0.012 μM/l | 0.8 μM/l |
| D | 0.090 μM/l | 0.017 μM/l | 1.2 μM/l |

4. Acute toxicity

The acute toxicity of the substances being tested was determined as a guide on groups of 10 mice after oral administration of a single dose of 250 mg/kg (observation period: 14 days). At this dose, none of the animals died.

Moreover, the before-mentioned compound A, for example, inhibits collagen-induced thrombocyte aggregation, thromboxane synthetase and thromboxane agonistic activity ex vivo in rats following oral administration of 10 mg/kg from more than 6 hours, whereby plasma levels up to 2800 ng pro ml blood are obtained which were estimated by means of a radio-receptor assay prepared with SQ 29,548-[5,6-3H(N)] (code NET-936).

In view of their pharmacological properties, the new compounds and the physiologically acceptable addition salts thereof are suitable for the treatment and prevention of thromboembolic disorders such as coronary infarct, cerebral infarct, so-called transient ischaemic attacks, Amaurosis fugax and for the prevention of arteriosclerosis and metastasis and for treating ischaemia, asthma and allergies.

The new compounds and the physiologically acceptable addition salts thereof are also suitable in the treatment of diseases involving thromboxane-mediated constriction or $PGE_2$-mediated dilation of the capillaries, e.g. in pulmonary hypertension. Moreover, these may be used to reduce the severity of a transplant rejection, in order to decrease the renal toxicity of substances such as cyclosporin, in order to treat kidney diseases, more particularly for the therapy or prevention of kidney changes connected with hypertension, systemic lupus or ureter blockages and in cases of shock in conjunction with sepsis, trauma or burns.

The dose reguired to achieve such an effect is expediently 0.3 to 4 mg/kg of body weight, preferably 0.3 to 2 mg/kg of body weight, two to four times a day. For this purpose, the compounds of formula I according to the invention, optionally combined with other active substances, may be made into conventional galenic preparations such as tablets, coated tablets, capsules, powders, suspensions or suppositories, by the use of one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetyl stearyl alcohol, carboxymethylcellulose or fatty substances such as hard fat or suitable mixtures thereof.

The present invention further relates to new pharmaceutical compositions containing a compound of formula I prepared according to the invention and a PDE-inhibitor or a lysing agent.

Examples of PDE-inhibitors include: 2,6-bis(diethanolamino)-4,8-dipiperidino-pyrimido[5,4-d]pyrimidine (Dipyridamole), 2,6-bis(diethanolamino)-4-piperidino-pyrimido[5,4-d]-pyrimidine (Mopidamole), 2-(4-methoxy-phenyl)-5(6)-(5-methyl-3-oxo-4,5-dihydro-2H-6-pyridazinyl)-benzimidazole (Pimobendane), 2-(4-hydroxy-phenyl)-5(6)-(5-methyl-3-oxo-4,5-dihydro-2H-6-pyridazinyl)-benzimidazole, 1-(1-oxido-thiomorpholino)-3-piperazino-5-methyl-isoguinoline, 6-[4-(3,4-dichlorophenylsulphinyl)-butoxy]-3,4-dihydrocarbostyrile and 6-[4-(2-pyridylsulphonyl)-butoxy]carbostyrile, whilst the oral daily dose for dipyridamole is 2.5 to 7.5 mg/kg, preferably 5 mg/kg, for mopidamole it is 15 to 25 mg/kg, preferably 20 mg/kg, for 2-(4-methoxy-phenyl)-5(6)-(5-methyl-3-oxo-4,5-dihydro-2H-6-pyridazinyl)-benzimidazole it is 0.05 to 0.15 mg/kg, preferably 0.08 to 0.10 mg/kg, for 2-(4-hydroxy-phenyl)-5(6)-(5-methyl-3-oxo-4,5-dihydro-2H-6-pyridazinyl)-benzimidazole it is 0.05 to 0.15 mg/kg, preferably 0.08 to 0.10 mg/kg, for 1-(1-oxido-thiomorpholino)-3-piperazino-5-methylisoquinoline it is 0.20 to 2.00 mg/kg, preferably 0.40 to 1.00 mg/kg, for 6-[4-(3,4-dichlorophenylsulphinyl)-butoxy]-3,4-dihydrocarbostyrile it is 0.10 to 1.00 mg/kg, preferably 0.20 to 0.50 mg/kg and for 6-[4-(2-pyridylsulphonyl)-butoxy]carbostyrile it is 0.10 to 1.00 mg/kg, preferably 0.20 to 0.50 mg/kg, and suitable lysing agents are plasminogen activators such as t-PA, rt-PA, streptokinase, eminase or urokinase, whilst the lysing agents may be administered parenterally but are preferably given by intravenous route, e.g. t-PA or rt-PA is given in a dosage of between 15 and 100 mg per patient, urokinase is given in a dose between 250,000 and 3,000,000 units per patient, eminase is given in a dose of about 30 mg per patient and streptokinase is given in a dose of between $5 \times 10^4$ and $3 \times 10^7$ IU within 5 minutes and 24 hours, respectively.

For pharmaceutical use, a new combination containing 1 to 500 mg of a PDE-inhibitor, preferably 2 to 75 mg, together with 10 to 300 mg, preferably 10 to 300 mg, of a compound of formula I prepared according to the invention and the physiologically acceptable addition salts thereof incorporated together with one or more inert conventional carriers and/or diluents, e.g. corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories. These are administered to adults 2 to 4 times a day, preferably 3 to 4 times a day, in order to achieve the desired effect.

Moreover, for pharmaceutical use, there is a new combination containing a lysing agent in the dosages mentioned above together with 10 to 300 mg, preferably 10 to 200 mg, of a compound of formula I prepared according to the invention and the physiologically acceptable addition salts thereof incorporated into conventional parenteral preparations, preferably conventional intravenous preparations such as ampoules or infusions, which dosage may be administered within 5 minutes and 24 hours.

Obviously, the individual active substances of the above-mentioned combinations may also be administered, if desired.

The Examples which follow illustrate the invention:
Preparation of the starting products:

EXAMPLE I

Methyl 6-(4-aminophenyl)-6-(3-pyridyl)-hex-5-enoate a) 4-Acetylaminophenyl-3-pyridyl-ketone 980 g of aluminium trichloride are slowly mixed with 155 ml of dimethylformamide. 342 g of nicotinic acid chloridehydrochloride and 206 g of N-acetylaniline are added successively to this mixture at 90 to 110° C. The reaction mixture is then mixed with 600 ml of ethylene chloride, then poured onto ice and neutralised by the addition of 15 N sodium hydroxide solution, with cooling. The agueous phase is extracted with methylene chloride. The combined organic phases are concentrated by evaporation and the residue is recrystallised from methanol.

Yield: 44% of theory
Melting point: 189°-191° C.
$C_{14}H_{12}N_2O_3$ (240.26) Calculated: C 69.99 H 5.03, N 11.66; Found: 69.87, 5.14, 11.58.

b) 6-(4-Acetylaminoohenyl)-6-(3-pyridyl)-hex-5-enoic acid

At −40° C., 140 g of 4-acetylaminophenyl-3-pyridyl-ketone are added to a suspension of 307 g of 4-carboxybutyl-triphenylphosphonium bromide and 233 g of potassium tert.butoxide in 2.8 litres of tetrahydrofuran and the mixture is stirred for 2 hours. The reaction mixture is decomposed by the addition of ice water and evaporated down. The residue is taken up in water and washed with ethyl acetate. The agueous phase is acidified to pH 5 to 6 and extracted with ethyl acetate. The organic phase is evaporated down and the residue is recrystallised from ethyl acetate/diisopropylether.

Yield: 86% of theory
Melting point: 155°-156° C.
$C_{19}H_{20}N_2O_3$ (324.38) Calculated: C 70.35, H 6.21, N 8.64 Found: 70.19, 6.27, 8.66.

c) Methyl 6-(4-aminophenyl)-6-(3-pyridyl)-hex-5-enoate 65 g of 6-(4-acetylaminophenyl)-6-(3-pyridyl)-hex-5-enoic acid are refluxed for 2 hours in a mixture of 300 ml of methanol and 150 ml of saturated methanolic hydrochloric acid. The reaction mixture is mixed with 500 ml of water, neutralised by the addition of sodium carbonate and extracted with ethyl acetate. The organic phase is washed, dried and evaporated down.

Yield: 71% of theory
Oil, $R_f$ value: 0.72 (silica gel; methylene chloride/acetone=9:1)
$C_{18}H_{20}N_2O_2$ (296.37); Calculated: C 72.95, H 6.80, N 9.45; Found: 72.83, 6.85, 9.23.

The following compound is obtained analogously to Example I:

methyl 6-(4-methylaminophenyl)-6-(3-pyridyl)-hex-5-enoate Oil, $R_f$ value: 0.56 (silica gel; methylene chloride/ethanol=20:1) .

$C_{19}H_{22}N_2O_2$ (310.40); Calculated: C 73.52, H 7.14, N 9.03; Found: 73.35, 7.24, 8.9.

EXAMPLE II

Methyl 6-(3-aminophenyl)-6-(3-pyridyl)-hex-5-enoate a) 3-Acetylaminophenyl-3-pyridylketone 114 g of 3-nitrophenyl-3-pyridylketone are hydrogenated in 1,000 ml of acetic acid and 35 g of Raney nickel for 2 hours at 50° C. under 5 bar of pressure. The catalyst is filtered off and the filtrate is mixed with 80 ml of acetic acid anhydride. After 30 minutes at ambient temperature the mixture is evaporated down and the residue is taken up in ethyl acetate. The organic phase is washed with aqueous potassium carbonate solution and dried pyer sodium sulphate. The solvent is rempyed and the residue is recrystallised from ethyl acetate/diisopropylether.

Yield: 69% of theory
Melting point: 116°–117° C.
$C_{14}H_{12}N_2O_2$ (240.26);
Calculated: C 69.99, H 5.03, N 11.66;
Found: 70.01, 5.11, 11.81.

b) 6-(3-Acetylaminophenyl)-6-(3-pyridyl)-hex-5-enoic acid

At −25° C., 94 g of 3-acetylaminophenyl-3-pyridylketone are added to a mixture of 217 g of 4-carboxybutyl-triphenylphosphonium bromide and 154 g of potassium tert.butoxide in 1.8 litres of tetrahydrofuran. After 2 hours stirring at ambient temperature, 200 ml of water are added to the reaction mixture and then it is evaporated down. The residue is taken up in 500 ml of water and washed with ethyl acetate. The agueous phase is then neutralised by the addition of citric acid and extracted with ethyl acetate. The organic phase is evaporated down and the residue is recrystallised from ethyl acetate/acetone.

Yield: 85% of theory
Melting point: 86°–89° C.
$C_{19}H_{20}N_2O_3$ (324.38); Calculated: C 70.35. H 6.21, N 8.64; Found: 70.15, 6.36, 8.50.

c) Methyl 6-(3-aminophenyl)-6-(3-pyridyl)-hex-5-enoate 65 g of 6-(3-acetylaminophenyl)-6-(3-pyridyl)-hex-5-enoic acid are refluxed for 4 hours in a mixture of 400 ml of methanol and 200 ml of methanolic hydrochloric acid. The solvent is eliminated and the residue is taken up in water. The agueous phase is washed with ethyl acetate and adjusted to pH 8–9 by adding 4N sodium hydroxide solution. The agueous phase is extracted with ethyl acetate. The organic phase is washed, dried and concentrated by evaporation.

Yield: 71% of theory
Oil, $R_f$ value: 0.55 (silica gel; methylene chloride/ethanol = 9:1)
$C_{18}H_{20}N_2O_2$ (296.37); Calculated: C 72.95, H 6.80 N 9.45; Found: 72.83, 6.91, 9.18.

The following compounds are obtained analogously to Example II:

Methyl 5-(3-aminophenyl)-5-(3-pyridyl)-pent-4-enoate

Resin, $R_f$ value: 0.58 (silica gel; methylene chloride/ethanol = 20:1)
$C_{17}H_{18}N_2O_2$ (282.34), Calculated: C 72.32, H 6.43, N 9.92; Found: 72.29, 6.55, 9.70.

Methyl 7-(3-aminophenyl)-7-(3-pyridyl)-hept-6-enoate

Resin, $R_f$ value: 0.63 (silica gel; methylene chloride/ethanol = 20:1)
$C_{19}H_{22}N_2O_2$ (310.40) Calculated: C 73.52, H 7.14, N 9.03; Found: 73.4, 7.18, 8.89.

EXAMPLE III

Methyl 6-(3-methylaminophenyl)-6-(3-pyridyl)-hex-5-enoate a) N-Aoetvl-3-methylaminophenyl-3-pyridylketone 17 g of sodium hydride followed by 22 ml of methyliodide are added in batches, with cooling, to 84 g of 3-acetylaminophenyl-3-pyridylketone in 600 ml of dimethylformamide. The mixture is stirred for one hour at ambient temperature and decomposed by the addition of 100 ml of water. The solvent is eliminated and the residue is taken up in ethyl acetate. The organic phase is washed, dried and evaporated down. The residue is purified pyer a silica gel column with methylene chloride/ethanol (30:1).

Oil, $R_f$ value: 0.45 (silica gel; methylene chloride/ethanol = 30:1)
$C_{15}H_{14}N_2O_2$ (254.29) Calculated: C 70.85, H 5.55, N 11.02; Found: 70.96, 5.65, 10.92.

b) Methyl 6-(3-methylaminophenyl)-6-(3-pyridyl)-hex-5-enoate

Prepared from N-acetyl-3-methylaminophenyl-3-pyridyl-ketone and 4-carboxybutyl-triphenylphosphonium bromide analogously to Example IIb and subseguent esterification analogously to Example IIc.

Oil, $R_f$ value: 0.56 (silica gel; methylene chloride/ethanol = 20:1).
$C_{19}H_{22}N_2O_2$ (310.40) Calculated: C 73.52, 7.14, N 9.03. Found: 73.53, 7.20, 8.84.

EXAMPLE IV (+)-E-2-(4-Chlorophenyl)-cyclopropane-1-carboxylic acid a) Ethyl E/Z-2-(4-chlorophenyl)-cyclopropane-1-carboxylate A mixture of 85 g of ethyl diazoacetate and 100 g of 4-chlorostyrene is added dropwise, within 2 hours, to 350 ml of boiling xylene. The mixture is heated for a further hour to 120° C. and the solvent is eliminated in vacuo. The residue is fractionated under a high vacuum.

Yield: 43% of theory,
Boiling point: 105°–112° C. (0.05 Torr)
$C_2H_{13}ClO_2$ (224.69) Calculated: C 64.15, H 5.83 Found: 64.33, 6.03 b) E-2-(4-Chlorophenyl)-cyclopropane-1-carboxylic acid and Z-2-(4-chloroohenyl)-cyclopropane-1-carboxylic acid Within 5 hours, 160 ml of water are added dropwise to a boiling mixture of 69 g of ethyl E/Z-2-(4-chlorophenyl)-cyclopropane-1-carboxylate and 8.8 g of sodium hydroxide in 180 ml of ethanol and 50 ml of water, and at the same time 150 ml of ethanol are distilled off. Then the ethyl Z-2-(4-chlorophenyl)-cyclopropane-1-carboxylate is extracted from the reaction mixture using ethyl acetate. The agueous phase is made alkaline and extracted with ethyl acetate. The organic phase is evaporated down and the residue is recrystallised from petroleum ether, producing 20 g of E-2-(4-chlorophenyl)-cyclopropane-1-carboxylic acid.

The organic phase which contains ester is evaporated down and the residue is heated to boiling in a mixture of 8.8 g of sodium hydroxide, 180 ml of ethanol and 50 ml of water. 160 ml of water are added dropwise within 5 hours to the boiling reaction mixture and at the same time 150 ml of ethanol are distilled off. Then the reaction solution is acidified and extracted with ethyl acetate. The organic phase is evaporated down and the residue is recrystallised from petrol/ethyl acetate, to yield 10.1 g of Z-2-(4-chlorophenyl)-cyclopropane-1-carboxylic acid.

Melting point (E-isomer): 116°–117° C.
Melting point (Z-isomer): 128°–129° C.
$C_{10}H_{19}ClO_2$ (196.63) Calculated: C 61.08, H 4.61 Found: (E-isomer): 60.96, 4.66; Found: (Z-isomer): 61.02, 4.76.

c) (+)- and
(−)-E-2-(4-chlorophenyl)-cyclopropane-1-carboxylic acid L-phenyl-glycinolamide At −55° C., 1.35 g of isobutylchloroformate are added dropwise to a mixture of 1.96 g of E-2-(4-chlorophenyl)-cyclopropane-1-carboxylic acid and 1.01 g of N-methyl-morpholine in 30 ml of tetrahydrofuran. After 10 minutes, 1.37 g of L-phenylglycinol are added and the mixture is heated to ambient temperature. After 2 hours the reaction mixture is combined with 30 ml of water, evaporated down and the precipitate formed is suction filtered. The product obtained is separated into the diastereomers by column chromatography on silica gel using methylene chloride/acetone (15:1). The pure fractions are subseguently recrystallised from ethyl acetate.

Yield: 30% of theory of diastereomer A and 26% of theory of diastereomer B $C_{18}H_{18}ClNO_2$ (315.80)

Calculated: C: 68.46, H 5.74, N 4.44; Found: (diastereomer A): 68.59, 5.86, 4.57 Found: (diastereomer B): 68.27, 5.81, 4.54.

d)
(+)-E-2-(4-Chlorophenyl)-cyclopropane-1-carboxylic acid 19 g of diastereomer A are dissglyed in 200 ml of dioxane and 200 ml of 4N hydrochloric acid and refluxed for 4 hours. The reaction mixture is evaporated down, the precipitate formed is suction filtered and recrystallised from petroleum ether/ethyl acetate.

Yield: 91% of theory
Melting point: 114°–115° C.
Specific rotation: α[D/20]=+351° (c=1.2; chloroform)
$C_{10}H_9ClO_2$ (196.63); Calculated: C 61.08, H 4.61 Found: 61.12, 4.64.

The following compounds are obtained analogously to Example IV:
(−)-E-2-(4-chlorophenyl)-cyclopropane-1-carboxylic acid
Melting point: 114°–115° C.
Specific rotation: α[D/20]=−348° (c=1.2; chloroform),
$C_{10}H_9ClO_2$ (196.63); Calculated: C 6.08, H 4.61 Found: 61.12, 4.55.

(+)-Z-2-(4-chlorophenyl)-cyclopropane-1-carboxylic acid
Melting point: 95°–96° C.
Specific rotation: α[D/20]=+2.6° (c=1.2; chloroform)
$C_{10}H_9ClO_2$ (196.63) Calculated: C 61.08, H 4.61; Found: 61.09, 4.64.

(−)-Z-2-(4-chlorophenyl)-cyclopropane-1-carboxylic acid
Melting point: 95°–96° C.
Specific rotation: α[D/20]=−2.6° (c=1.2; chloroform)
$C_{10}H_9ClO_2$ (196.63); Calculated: C 61.08, H 4.61; Found: 61 24, 4.64.

Preparation of the end products:

EXAMPLE 1

6-[4-(4-Methylbenzenesulphonylamino)-phenyl]-6-(3-pyridyl)-hex-5-enoic acid

A mixture of 3 g of methyl 6-(4-aminophenyl)-6-(3-pyridyl)-hex-5-enoate, 1.9 g of 4-methylbenzene-sulphonic acid chloride and 5 ml of triethylamine in 100 ml of methylene chloride is stirred for one hour at ambient temperature. The organic phase is washed with water, evaporated down and the residue is purified pyer a silica gel column with ethyl acetate. The product fraction is evaporated down and heated in a mixture of 50 ml of ethanol and 3 ml of 10N sodium hydroxide solution to 50° C. for one hour. The reaction mixture is diluted with water and neutralised by the addition of citric acid. The agueous phase is extracted with ethyl acetate, dried and evaporated down. The residue is recrystallised from ethyl acetate/diisopropylether.

Yield: 53% of theory
Melting point: 110°–111° C.
$C_{24}H_{24}N_2O_4S$ (436.53); Calculated: C 66.04, H 5.54, N 6.42; Found: 65.98, 5.74, 6.25.

The following compounds are obtained analogously to Example 1:

6-[4-(4-fluorobenzenesulphonylamino)-phenyl]-6-(3-pyridyl)-hex-5-enoic acid
Melting point: 95°–96° C.
$C_{23}H_{21}FN_2O_4S$ (440.50) Calculated: C 62.71, H 4.81, N 6.36; Found: 62.51, 5.02, 6.15.

6-[4-(4-chlorobenzenesulphonylamino)-phenyl]-6-(3-pyridyl)-hex-5-enoic acid
Melting point: 109°–111° C.
$C_{23}H_{21}ClN_2O_4S$ (456.95); Calculated: C 60.45, H 4.63, N 6.13; Found: 60.23, 4.83, 5.96.

6-[4-(4-trifluoromethylbenzenesulphonylamino)-phenyl]-6-(3-pyridyl)-hex-5-enoic acid
Melting point: 116°–117° C.
$C_{24}H_{21}F_3N_2O_4S$ (490.50). Calculated: C 58.77, H 4.32, N 5.71; Found: 58.68, 4.56, 5.67.

6-[4-(4-methoxybenzenesulphonylamino)-phenyl]-6-(3-pyridyl)-hex-5-enoic acid
Melting point: 129°–130° C. $C_{24}H_{24}N_2O_5S$ (452.53); Calculated: C 63.70, H 5.35, N 6.19; Found: 63.89, 5.42, 6.34.

6-[4-(4-amino-3,5-dichlorobenzenesulphonylamino)-phenyl]-6-(3-pyridyl)-hex-5-enoic acid
Melting point: 233° C.
$C_{23}H_{21}Cl_2N_3O_4S$ (506.41) Calculated: C54.55, H 4.18, N 8.30; Found: 54.41, 4.26, 8.16.

6-[4-(2-naphthalenesulphonylamino)-phenyl]-6-(3-pyridyl)-hex-5-enoic acid
Melting point: 177°–178° C.
$C_{27}H_{24}N_2O_4S$ (472.57); Calculated: C 68.63, H 5.12, N 5.93; Found: 68.45, 4.92, 5.87.

6-[4-(2-(5-chlorothienyl)-sulphonylamino)-phenyl]-6-(3-pyridyl)-hex-5-enoic acid
Melting point: 139°–141° C.
$C_{21}H_{19}ClN_2O_4S_2$ (462.97); Calculated: C 54.48, H 4.14, N 6.05; Found: 54.34, 4.06, 6.20.

6-(4-benzenesulphonylaminophenyl)-6-(3-pyridyl)-hex-5-enoic acid
Melting point: 149°–151° C.
$C_{23}H_{22}N_2O_4S$ (422.51) Calculated: C 65.38, H 5.25, N 6.63; Found: 65.27, 5.10, 6.57.

6-[4-(1-n-butylsulphonylamino)-phenyl]-6-(3-pyridyl)-hex-5-enoic acid
Melting point: 65° C.
$C_{21}H_{26}N_2O_4S$ (402.51); Calculated: C 62.66 ; H 6.51, N 6.96; Found: 62.51, 6.69, 6.84.

6-[3-(4-chlorobenzenesulphonylamino)-phenyl]-6-(3-pyridyl)-hex-5-enoic acid
Melting point: 187°–188° C.

$C_{23}H_{21}ClN_2O_4S$ (456.95); Calculated: C 60.46, H 4.63, N 6.13; Found: 60.64, 4.87, 5.96.

6-[3-(I-naphthalenesulphonylamino)-phenyl]-6-(3-pyridyl)-hex-5-enoic acid

Melting point: 208°–209° C.

$C_{27}H_{24}N_2O_4S$ (472.56); Calculated: C 68.63, H 5.12, N 5.93; Found: 68.48, 5.13, 5.96.

6-[3-(2-naphthalenesulphonylamino)-phenyl]-6-(3-pyridyl)-hex-5-enoic acid

Melting point: 185°–186° C.

$C_{27}H_{24}N_2O_4S$ (472.56) Calculated: C 68.63, H 5.12, N 5.93; Found: 68.50, 5.30, 5.90.

EXAMPLE 2

6-[4-(N-Isopropyl-4-chlorobenzenesulphonylamino)-phenyl]-6-(3-pyridyl)-hex-5-enoic acid a) Methyl 6-(4-isopropylaminophenyl)-6-(3-pyridyl)-hex-5-enoate 6 g of methyl 6-(4-aminophenyl)-6-(3-pyridyl)-hex-5-enoate, 2.7 g of isopropylbromide, 5 ml of triethylamine and 0.5 g of sodium iodide are heated to 90° C. in 60 ml of dimethylformamide for 18 hours. The reaction mixture is evaporated down, the residue is taken up in water and extracted with ethyl acetate. The organic phase is evaporated down and the residue is chromatographed pyer a silica gel column using ethyl acetate.

Yield: 27% of theory

Resin, $R_f$ value: 0.35 (silica gel; methylene chloride/acetone=9:1).

$C_{21}H_{26}N_2O_4$ (338.45); Calculated: C 74.53, H 7.74, N 8.28; Found: 74.52, 7.92, 8.02.

b) 6-[4-(N-Isopropyl-4-chlorobenzenesulphonylamino)-phenyl]-6-(3-pyridyl)-hex-5-enoic acid Prepared by saponification of methyl 6-[4-(N-isopropyl-4-chlorobenzenesulphonylamino)-phenyl]-6-(3-pyridyl)-hex-5-enoate using 10N sodium hydroxide solution analogously to Example 1.

Yield: 41% of theory

Melting point: 169°–170° C.

$C_{26}H_{27}ClN_2O_4S$ (499.03); Calculated: C 62.58; H 5.45; N 5.61; Found: 62.42, 5.52, 5.44.

EXAMPLE 3

7-[4-(4-Chlorobenzenesulphonylamino)-phenyl]-7-(3-pyridyl)-hept-6-enoic acid a) 4-(4-Chlorobenzenesulohonylamino)-henyl-3-pyridyl-ketone 24 g of 4-acetylaminophenyl-3-pyridyl-ketone are refluxed for 2 hours in 100 ml of 6N hydrochloric acid. The reaction mixture is evaporated down and the residue is suspended in 300 ml of methylene chloride. 21 g of 4-chlorobenzenesulphonic acid chloride and 60 ml of triethylamine are added successively to this suspension and stirred for 2 hours at ambient temperature. The reaction mixture is washed with water, dried and evaporated down. The residue is purified pyer a silica gel column with methylene chloride/acetone (19:1) and then recrystallised from ethanol.

Yield: 40% of theory

Melting point: 196° C.

$C_{18}H_{13}ClN_2O_3S$ (372.83); Calculated: C 57.99, H 3.51, N 7.51; Found: 57.88, 3.57, 7.69.

b) 7-4-(4-Chlorobenzenesulphonylamino)-ohenv11-7-(3-pyridyl)-hept-6-enoic acid

At −30° C., 5.95 g of 3-carboxypropyl-triphenyl-phosphonium bromide, 4 g of potassium tert.butoxide and 3.7 g of 4-(4-chlorobenzenesulphonylamino)-phenyl-3-pyridyl-ketone are added successively to 150 ml of tetrahydrofuran. The mixture is stirred for one hour at ambient temperature. The reaction mixture is evaporated down, the residue is taken up in water and washed with ethyl acetate. The agueous phase is neutralised by the addition of citric acid and extracted with ethyl acetate/ethanol (9:I). The organic phase is evaporated down and the residue is recrystallised from methylene chloride/diisopropylether.

Yield: 64% of theory

Melting point: 186°–187° C.

$C_{24}H_{23}ClN_2O_4S$ (470.98); Calculated: C 61.21, H 4.92, N 5.95; Found: 61.14, 4.91, 5.77.

The following compound is obtained analogously to Example 3:

5-[4-(4-chlorobenzenesulphonylamino)-phenyl]-5-(3-pyridyl)-pent-4l -enoic acid

Yield: 33% of theory

Melting point: 151°–152° C.

$C_{22}H_{19}ClN_2O_4S$ (442.93); Calculated: C 59.65, H 4.32, N 6.32; Found: 59.42, 4.37, 6.16.

EXAMPLE 4

6-[4-(4-Methylbenzenesulphonylamino)-phenyl]-6-(3-pyridyl)-hexanoic acid 1 g of 6-[4-(4-methylbenzenesulphonylamino)-phenyl]-6-(3-pyridyl)-hex-5-enoic acid is dissglyed in a mixture of 20 ml of methanol and 5 ml of 1N sodium hydroxide solution. After the addition of 200 mg of palladium catalyst (10% on charcoal) the mixture is hydrogenated under 5 bar. Then the catalyst is filtered off, the filtrate is neutralised with IN hydrochloric acid and evaporated down. The residue is taken up in ethyl acetate, decocted with activated charcoal, filtered and evaporated down.

Yield: 74% of theory

Foam, $R_f$ value: 0.58 (silica gel; ethyl acetate)

$C_{24}H_{26}N_2O_4S$ (438.55) Calculated: C 65.73, H 5.98, N 6.39; Found: 65.58, 6.07, 6.35.

EXAMPLE 5

6-[4-(4-Chlorobenzoylamino)-phenyl]-6-(3-pyridyl)-hex-5-enoic acid

At 5°–10° C., 5 ml of triethylamine are added dropwise to a mixture of 3 g of methyl 6-(4-aminophenyl)-6-(3-pyridyl)-hex-5-enoate and 2.1 g of 4-chlorobenzoic acid chloride. After 30 minutes the reaction mixture is washed with water and evaporated down. The residue is mixed with 30 ml of ethanol and 5 ml of 10N sodium hydroxide solution and heated to 50° C. for 30 minutes. The reaction mixture is evaporated down and the residue is taken up in water. The agueous phase is washed with ethyl acetate, neutralised by the addition of citric acid and then extracted with ethyl acetate. The organic phase is washed with water, dried and evaporated down and the residue is recrystallised from ethyl acetate/diisopropylether.

Yield: 64% of theory

Melting point: 94°–95° C.

$C_{24}H_{21}ClN_2O_3$ (420.90) Calculated: C 68.49, H 5.03, N 6.60.

Found: 68.21, 5.13, 6.60.

The following compounds are obtained analogously to Example 5:

6-[4-(1-naphthoylamino)-phenyl]-6-(3-pyridyl)-hex-5-enoic acid

Melting point: 227° C.

$C_{28}H_{24}N_2O_3$ (436.51); Calculated: C 77.04, H 5.54, N 6.42; Found: 76.83, 5.53, 6.31.

6-[4-(3-chlorobenzoylamino)-phenyl]-6-(3-pyridyl)-hex-5-enoic acid

Melting point: 180°–182° C.

$C_{24}H_{21}ClN_2O_3$ (420.90); Calculated: C 68.49, H 5.03, N 6.66; Found: 68.34, 5.02, 6.75.

6-(4-phenylacetylaminophenyl)-6-(3-pyridyl)-hex-5-enoic acid

Melting point: 168°–169° C.

$C_{25}H_{24}N_2O_3$ (400.48) Calculated: C 74.98, H 6.03, N 6.99; Found: 74.85, 6.25, 7.02.

6-[4-(2-phenylbenzoylamino)-phenyl]-6-(3-pyridyl)-hex-5-enoic acid

Melting point: 182°–183° C.

$C_{30}H_{26}N_2O_3$ (462.55); Calculated: C 77.90, H 5.67, N 6.06; Found: 77.80, 5.89, 6.18.

6-[4-(I-(4-chlorophenyl)-cyclopropylcarboxamido)-phenyl]-6-(3-pyridyl)-hex-5-enoic acid Melting point: 147°–148° C.

$C_{27}H_{25}ClN_2O_3$ (460.96); Calculated: C 70.35, H 5.47, N 6.08; Found: 70.54, 5.46, 6.06.

6-[4-(E-m-chlorocinnamoylamino)-phenyl]-6-(3-pyridyl)-hex-5-enoic acid

Melting point: 101°–102° C.

$C_{26}H_{23}ClN_2O_3$ (446.93); Calculated: C 69.87; H 5.19, N 6.27; Found: 69.79, 5.37, 6.53.

6-[4-(3-(4-chlorophenyl)-propionylamino)-phenyl]-6-(3-pyridyl)-hex-5-enoic acid

Melting point: 148° C.

$C_{26}H_{25}ClN_2O_3$ (448.95); Calculated: C 69.56, H 5.61, N 6.24; Found: 69.45, 5.62, 6.41.

6-[4-(4-chlorophenylacetylamino)-phenyl]-6-(3-pyridyl)-hex-5-enoic acid

Melting point: 176°–177° C.

$C_{25}H_{23}ClN_2O_3$; Calculated: C 69.04, H 5.33, N 6.44; Found: 68.93, 5.51, 6.31.

6-[4-(4-phenylbutanoylamino)-phenyl]-6-(3-pyridyl)-hex-5-enoic acid

Melting point: 144°–145° C.

$C_{27}H_{28}N_2O_3$ (428.53); Calculated: C 75.68, H 6.59, N 6.54; Found: 75.64, 6.72, 6.45.

6-[4-(3-phenylpropynoylamino)-phenyl]-6-(3-pyridyl)-hex-5-enoic acid

Melting point: 95°–96° C.

$C_{26}H_{22}N_2O_3$ (410.47); Calculated: C 76.08, H 5.40 N 6.83; Found: 75.85, 5.60, 6.95.

6-[4-(E-2-phenylcyclopropyl-1-carboxamido)-phenyl]-6-(3-pyridyl)-hex-5-enoic acid Melting point: 175°–176° C.

$C_{27}H_{26}N_2O_3$ (426.51) Calculated: C 76.09, H 6.14, N 6.56; Found: 76.06, 6.18, 6.48.

(+)-5E-6-[4-(E-2-(4-chlorophenyl)-cyclopropyl-1-carboxamido)phenyl]-6-(3-pyridyl)-hex-5-enoic acid Melting point: 167°–168° C.

Specific rotation: $\alpha[D/20] = +292°$ (c=1.2; methanol)

$C_{27}H_{25}ClN_2O_3$ (460.96); Calculated: C 70.35, H 5.47, N 6.07; Found: 70.18, 5.56, 6.11.

(−)-5E-6-[4-(E-2-(4-chlorophenyl)-cyclopropyl-1-carboxamido)phenyl]-6-(3-pyridyl)-hex-5-enoic acid Melting point: 167°–168° C.

Specific rotation: $\alpha[D/20] = -294°$ (c=1.2; methanol)

$C_{27}H_{25}ClN_2O_3$ (460.96) Calculated: C 70.35, H 5.47, N 6.07; Found: 70.28, 5.56, 6.00.

(+)-5E-6-[4-(Z-2-(4-chlorophenyl)-cyclopropyl-1-carboxamido)phenyl]-6-(3-pyridyl)-hex-5-enoic acid Melting point: 110°–111° C.

Specific rotation: $\alpha[D/20] = +10.5°$ (c=1.2; methanol).

$C_{27}H_{25}ClN_2O_3$ (460.96); Calculated: C 70.35, H 5.47, N 6.07; Found: 70.24, 5.62, 6.22.

(−)-5E-6-[4-(Z-2-(4-chlorophenyl)-cyclopropyl-1-carboxamido)phenyl]-6-(3-pyridyl)-hex-5-enoic acid Melting point: 110°–111° C.

Specific rotation: $\alpha[D/20] = -11°$ (c=1.2; methanol)

$C_{27}H_{25}ClN_2O_3$ (460.96); Calculated: C 70.35, H 5.4, N 6.07; Found: 70.20, 5.55, 6.07.

6-[4-(Z-2-(4-bromophenyl)-cyclopropyl-1-carboxamido)-phenyl]-6-(3-pyridyl)-hex-5-enoic acid Melting point: 204°–205° C.

$C_{27}H_{25}BrN_2O_3$ (505.41); Calculated: C 64.17, H 4.99, N 5.54; Found: 64.00, 5.01, 5.63.

6-[4-(Z-2-(4-chlorobenzoyl)-cyclopropyl-1-carboxamido)-phenyl]-6-(3-pyridyl)-hex-5-enoic acid Melting point: 193°–194° C.

$C_{27}H_{25}ClN_2O_4$ (488.96); Calculated: C 68.78, H 5.15, N 5.72; Found: 68.68, 5.23, 5.73.

6-[4-(N-methyl-3-(4-chlorophenyl)-propionylamino)-phenyl]-6-(3-pyridyl)-hex-5-enoic acid Melting point: 87°–90° C.

$C_{27}H_{27}ClN_2O_2$ (462.97); Calculated: C 70.05, H 5.88, N 6.05; Found: 69.95, 5.87, 5.95

6-[4-(N-methyl-Z-2-(4-chlorophenyl)-cyclopropyl-1-carboxamido)phenyl]-6-(3-pyridyl)-hex-5-enoic acid Foam, $R_f$ value: 0.41 (silica gel; methylene chloride/ethanol=20:1)

$C_{28}H_{27}ClN_2O_3$ (474.99); Calculated: C 70.80; H 5.73, N 5.90; Found: 70.71, 5.75, 5.66.

6-[4-(N-methyl-E-2-(4-chlorophenyl)-cyclopropyl-1-carboxamido)phenyl]-6-(3-pyridyl)-hex-5-enoic acid Melting point: 148°–150° C.

$C_{28}H_{27}ClN_2O_3$ (474.99); Calculated: C 70.80 H 5.73, N 5.90; Found: 70.60, 5.79, 5.80.

6-[3-(2-phenylbenzoylamino)-phenyl]-6-(3-pyridyl)-hex-5-enoic acid

Melting point: 214°–216° C.

$C_{30}H_{26}ClN_2O_3$ (462.55); Calculated: C 77.90; H 5.67, N 6.06; Found: 77.79, 5.86, 5.97;

6-[3-(E-p-chlorocinnamoylamino)-phenyl]-6-(3-pyridyl)-hex-5-enoic acid

Melting point: 173°–174° C.

$C_{26}H_{23}ClN_2O_3$ (446.93); Calculated: C 69.87 H 5.19 N 6.27; Found: 69.68, 5.27, 6.05.

6-[3-(4-chlorobenzoylamino)-phenyl]-6-(3-pyridyl)-hex-5-enoic acid

Melting point: 186° C.

$C_{24}H_{21}ClN_2O_3$ (420.90); Calculated: C 68.49 H 5.03, N 6.66; Found: 68.29, 5.14, 6.55.

6-[3-(3-chlorobenzoylamino)-phenyl]-6-(3-pyridyl)-hex-5-enoic acid

Melting point: 173° C.

$C_{24}H_{21}ClN_2O_3$ (420.90); Calculated: C 68.49, H 5.03, N 6.66; Found: 68.33, 5.13, 6.73.

6-[3-(E-o-chlorocinnamoylamino)-phenyl]-6-(3-pyridyl)-hex-5-enoic acid

Melting point: 199°–200° C.
$C_{26}H_{23}ClN_2O_3$ (446.93); Calculated: C 69.87 H 5.1 N 6.27; Found: 69.67, 5.15, 6.29.

6-[3-(E-m-chlorocinnamoylamino)-phenyl]-6-(3-pyridyl)-hex-5-enoic acid
Melting point: 187°–188° C.
$C_{26}H_{23}ClN_2O_3$ (446.93); Calculated: C 69.87, H 5.19 N 6.27; Found: 69.67, 5.29, 6.26.

6-[3-(2-naphthoylamino)-phenyl]-6-(3-pyridyl)-hex-5-enoic acid
Melting point: 207°–208° C.
$C_{27}H_{24}ClN_2O_3$ (424.50); Calculated: C 76.39 H 5.7, N 6.60; Found: 76.53, 5.64, 6.47.

6-[3-(4-methoxybenzoylamino)-phenyl]-6-(3-pyridyl)-hex-5-enoic acid
Melting point: 168°–170° C.
$C_{25}H_{24}ClN_2O_3$ (416.48); Calculated: C 72.10, H 5.81, N 6.73; Found: 71.99, 5.83, 6.80.

6-[3-(3-phenylpropionylamino)-phenyl]-6-(3-pyridyl)-hex-5-enoic acid
Melting point: 157° C.
$C_{26}H_{26}ClN_2O_3$ (414.50); Calculated: C 75.33, H 6.32, N 6.76; Found: 75.34, 6.35, 6.91.

6-[3-(4-phenylbenzoylamino)-phenyl]-6-(3-pyridyl)-hex-5-enoic acid
Melting point: 163°–164° C.
$C_{30}H_{26}ClN_2O_3$ (462.55); Calculated: C 77.90, H 5.67, N 6.06; Found: 77.83, 5.50, 6.13.

(+)-5E-6-[3-(E-2-(4-chlorophenyl)-cyclopropyl-1-carboxamido)phenyl]-6-(3-pyridyl)-hex-5-enoic acid
foam, $R_f$ value: 0.33 (silica gel; methylene chloride/ethanol=20:1)
Specific rotation: $\alpha[D/20] = +242°$ (c=1.2; methanol)
$C_{27}H_{25}ClN_2O_3$ (460.96). Calculated: C 70.35, H 5.47, N 6.07; Found: 70.28, 5.70, 5.83.

(−)-5E-6-[3-(E-2-(4-chlorophenyl)-cyclopropyl-1-carboxamido)phenyl]-6-(3-pyridyl)-hex-5-enoic acid foam, $R_f$ value: 0.33 (silica gel; methylene chloride/ethanol=20:1)
Specific rotation: $\alpha[D/20] = -243°$ (c=1.2; methanol)
$C_{27}H_{25}ClN_2O_3$ (460.96); Calculated: C 70.35, H 5.47, N 6.07; Found: 70.20, 5.67, 5.95.

(+)-5E-6-[3-(Z-2-(4-chlorophenyl)-cyclopropyl-1-carboxamido)phenyl]-6-(3-pyridyl)-hex-5-enoic acid
Melting point: 221°–222° C.
Specific rotation: $\alpha[D/20] = +87°$ (c=1.2; dimethylformamide)
$C_{27}H_{25}ClN_2O_3$ (460.96) Calculated: C 70.35, H 5.4, N 6.07; Found: 70.38, 5.53, 5.96.

(−)-5E-6-[3-(Z-2-(4-chlorophenyl)-cyclopropyl-1-carboxamido)phenyl]-6-(3-pyridyl)-hex-5-enoic acid
Melting point: 220°–221° C.
Specific rotation: $\alpha[D/20] = -87°$ (c=1.2; dimethylformamide)
$C_{27}H_{25}ClN_2O_3$ (460.96); Calculated: C 70.35, H 5.47, N 6.07; Found: 70.21, 5.48, 6.07.

6-[3-(E-2-(4-bromophenyl)-cyclopropyl-1-carboxamido)-phenyl]-6-(3-pyridyl)-hex-5-enoic acid
Melting point: 165°–168° C.
$C_{27}H_{25}ClN_2O_3$ (505.41); Calculated: C 64.17, H 4.99, N 5.54; Found: 64.00, 5.10, 5.69.

6-[3-(1-(4-chlorophenyl)-cyclopropylcarboxamido)-phenyl]-6-(3-pyridyl)-hex-5-enoic acid
Melting point: 149°–150° C.
$C_{27}H_{25}ClN_2O_3$ (460.96); Calculated: C 70.35, H 5.47, N 6.07; Found: 70.19, 5.59, 6.11.

6-[3-(3-(4-chlorophenyl)-propionylamino)-phenyl]-6-(3-pyridyl)-hex-5-enoic acid
Melting point: 163° C.
$C_{26}H_{25}ClN_2O_3$ (448.95); Calculated: C 69.56, H 5.61, N 6.24; Found: 69.56, 5.64, 6.40.

6-[3-(4-chlorophenylacetylamino)-phenyl]-6-(3-pyridyl)-hex-5-enoic acid
Melting point: 192°–193° C.
$C_{25}H_{23}ClN_2O_3$ (434.92); Calculated: C 69.04, H 5.33, N 6.44; Found: 68.87, 5.37, 6.48.

6-[3-(4-phenylbutanoylamino)-phenyl]-6-(3-pyridyl)-hex-5-enoic acid
Melting point: 116°–117° C.
$C_{27}H_{28}N_2O_3$ (428.53); Calculated: C 75.68, H 5.59, N 6.54; Found: 75.69, 5.70, 6.42.

6-[3-(4-phenylpropynoylamino)-phenyl]-6-(3-pyridyl)-hex-5-enoic acid
Melting point: 159°–160° C.
$C_{26}H_{22}N_2O_3$ (410.47); Calculated: C 76.08, H 5.40, N 6.83; Found: 75.96, 5.50, 7.03.

6-[3-(Z-2-(4-bromophenyl)-cyclopropyl-1-carboxamido)-phenyl]-6-(3-pyridyl)-hex-5-enoic acid
Melting point: 204°–205° C.
$C_{27}H_{25}BrN_2O_3$ (505.41); Calculated: C 64.17, H 4.99, N 5.54; Found: 64.00, 5.01, 5.63.

6-[3-(4-chlorophenylsulphonylaminoacetylamino)-phenyl]-6-(3-pyridyl)-hex-5-enoic acid
Melting point: 110°–112° C.
$C_{25}H_{24}ClN_2O_3$ (514.00); Calculated: C 58.42, H 4.71, N 8.18; Found: 58.30, 4.81, 8.05.

6-[3-(3,3-diphenylpropionylamino)-phenyl]-6-(3-pyridyl)-hex-5-enoic acid
Foam, $R_f$ value: 0.30 (silica gel; methylene chloride/ethanol=20:1),
$C_{32}H_{30}N_2O_3$ (490.60) Calculated: C 78.34, H 6.16, N 5.71; Found: 78.21, 6.29, 5.67.

6-[3-(E-3,3-dichloro-2-(4-chlorophenyl)-cyclopropyl-1-carboxamido)-phenyl]-6-(3-pyridyl)-hex-5-enoic acid
Melting point: 65° C.
$C_{27}H_{23}Cl_3N_2O_3$ (529.85) ; Calculated: C 61.21, H 4.38, N 5.29; Found: 61.04, 4.54, 5.05.

6-[3-(N-methyl-E-o-chlorocinnamoylamino)-phenyl]-6-(3-pyridyl)-hex-5-enoic acid
Melting point: 128°–130° C.
$C_{27}H_{25}ClN_2O_3$ (460.96); Ca)culated: C 70.35, H 5.47, N 6.08; Found: 70.32, 5.43, 6.10.

-[3-(N-methyl-3-(4-chlorophenyl)-propionylamino)-phenyl]-6-(3-pyridyl)-hex-5-enoic acid
Oil, $R_f$ value; 0.73 (silica gel; methylene chloride/ethanol=9:1).
$C_{27}H_{27}ClN_2O_3$ (462.98); Calculated: C 70.05 H 5.88, N 6.05; Found: 69.88, 5.99, 5.88.

6-[3-(N-methyl-3-(2-chlorophenyl)-propionylamino)-phenyl]-6-(3-pyridyl)-hex-5-enoic acid
Melting point: 122°–124° C.
$C_{27}H_{27}ClN_2O_3$ (462.98); Calculated: C 70.05, H 5.88, N 6.05; Found: 69.85, 5.73, 6.04.

6-[3-(N-methyl-3,3-diphenylpropionylamino)-phenyl]-6-(3-pyridyl)-hex-5-enoic acid
Foam, $R_f$ value: 0.46 (silica gel; methylene chloride/ethanol=20:1).
$C_{33}H_{32}N_2O_3$ (504.63); Calculated: C 78.55; H 6.39, N 5.55; Found: 78.43, 6.49, 5.48.

6-[3-(N-methyl-3-(4-methoxyphenyl)-propionylamino)-phenyl]-6-(3-pyridyl)-hex-5-enoic acid
Melting point: 135° C.
$C_{28}H_{30}N_2O_3$ (458.56); Calculated: C 73.34, H 6.59, N 6.11; Found: 73.20, 6.70, 6.17.

6-[3-(N-methyl-3-phenylpropynoylamino)-phenyl]-6-(3-pyridyl)-hex-5-enoic acid

Melting point: 123°-125° C.

$C_{27}H_{24}ClN_2O_3$ (424.50); Calculated: C 76.40, H 5.70, N 6.60; Found: 76.30, 5.73, 6.88.

7-[3-(E-2-(4-chlorophenyl)-cyclopropyl-1-carboxamido)-phenyl]-7-(3-pyridyl)-hept-6-enoic acid Foam, $R_f$ value: 0.15 (silica gel; methylene chloride/acetone=9:1)

$C_{28}H_{27}ClN_2O_3$ (474.99) Calculated: C 70.80, H 5.73, N 5.90; Found: 70.64, 5.87, 6.00.

7-[3-(3-(4-chlorophenyl)-propionylamino)-phenyl]-7-(3-pyridyl)-hept-6-enoic acid Foam, $R_f$ value: 0.20 (silica gel; ethyl acetate)

$C_{27}H_{27}ClN_2O_3$ (462.98); Calculated: C 70.05, H 5.88, N 6.05; Found: 69.90, 5.90, 6.06.

5-[3-(E-2-(4-chlorophenyl)-cyclopropyl-1-carboxamido)-phenyl]-5-(3-pyridyl)-pent-4-enoic acid Foam, $R_f$ value: 0.22 (silica gel; methylene chloride/ethanol=19:1)

$C_{26}H_{25}ClN_2O_3$ (448.95); Calculated: C 69.56, H 5.61, N 6.24; Found: 69.37, 5.35, 6.22.

5-[3-(3-(4-chlorophenyl)-propionylamino)-phenyl]-5-(3-pyridyl)-pent-4-enoic acid Melting point: 200°-201° C.

$C_{25}H_{23}ClN_2O_3$ (434.92); Calculated: C 69.04, H 5.33, N 6.44; Found: 68.86, 5.39, 6.42.

EXAMPLE 6

6-[3-(4-Chlorophenoxyacetylamino)-phenyl]-6-(3-pyridyl)-hex-5-enoic acid 2.25 g of methyl 6-(3-aminophenyl)-6-(3-pyridyl)-hex-5-enoate are dissolved in 30 ml of methylene chloride. At 0° C., 1.65 g of 4-chlorophenoxyacetic acid chloride and 2.5 ml of triethylamine are added successively to this solution which is then stirred for 2 hours at ambient temperature. The reaction mixture is washed with water and then evaporated down. The residue is dissolved in a mixture of 20 ml of ethanol and 16 ml of 0.5N sodium hydroxide solution and stirred for 24 hours at ambient temperature. The reaction mixture is evaporated down at ambient temperature, water is added and the resulting mixture is washed with ethyl acetate. The aqueous phase is neutralised by the addition of citric acid and extracted with ethyl acetate. The organic phase is washed with water, dried and evaporated down and the residue is recrystallised from ethyl acetate/diisopropyl ether.

Yield: 49% of theory

Melting point: 178°-179° C.

$C_{25}H_{23}ClN_2O_3$ (450.92); Calculated: C 66.59, H 5.14: N 6.21; Found: 66.48, 5.29, 5.99.

The following compounds are obtained analogously to Example 6:

6-[3-(2-(4-chlorophenoxy)-isobutyroylamino)-phenyl]-6-(3-pyridyl)-hex-5-enoic acid Melting point: 92° C.

$C_{27}H_{27}ClN_2O_3$ (478.98); Calculated: C 67.71, H 5.68, N 5.85; Found: 67.56, 5.79, 5.67.

6-[3-(2-chlorophenoxyacetylamino)-phenyl]-6-(3-pyridyl)-hex-5-enoic acid

Melting point: 134°-136° C.

$C_{25}H_{23}ClN_2O_3$ (450.92); Calculated: C 66.59, H 5.14, N 6.21; Found: 66.51, 5.13, 6.16.

6-[3-(2,4-dichlorophenoxyacetylamino)-phenyl]-6-(3-pyridyl)-hex-5-enoic acid

Melting point: 148°-150° C.

$C_{25}H_{27}ClN_2O_3$ (485.37); Calculated: C 61.87, H 4.57, N 5.77; Found: 61.74, 4.45, 5.81.

6-[3-(N-methyl-2-chlorophenoxyacetylamino)-phenyl]-6-(3-pyridyl)-hex-5-enoic acid Melting point: 118°-119° C.

$C_{26}H_{25}ClN_2O_3$ (464.95); Calculated: C 67.17, H 5.42, N 6.02; Found: 66.99, 5.46, 5.99.

6-[3-(N-methyl-(2-chlorophenoxy)-isobutyroylamino)-phenyl]-6-(3-pyridyl)-hex-5-enoic acid Foam, $R_f$ value: 0.45 (silica gel; methylene chloride/ethanol=20:1)

$C_{28}H_{29}ClN_2O_3$ (493.00); Calculated: C 68.22, H 5.93, N 5.68; Found: 68.10, 6.09, 5.65.

6-[3-(N-methyl-4-chlorophenoxyacetylamino)-phenyl]-6-(3-pyridyl)-hex-5-enoic acid Melting point: 128°-132° C.

$C_{26}H_{25}ClN_2O_3$ (464.95); Calculated: C 67.17, H 5.42, N 6.02; Found: 67.26, 5.32, 6.13.

6-[3-(N-methyl-2,4-dichlorophenoxyacetylamino)-phenyl]-6-(3-pyridyl)-hex-5-enoic acid Melting point: 146° C.

$C_{26}H_{24}Cl_2N_2O_4$ (499.40). Calculated: C 62.53, H 4.84, N 5.61; Found: 62.47, 4.90, 5.40.

EXAMPLE 7

6-[3-(N-Methyl-3-(3-indolyl)-propionylamino)-phenyl]-6-(3-pyridyl)-hex-5-enoic acid A mixture of 1.9 g of 3-(3-indolyl)-propionic acid, 2.3 g of methyl 6-(3-methylaminophenyl)-6-(3-pyridyl)-hex-5-enoate and 1.8 g of carbonyldiimidazole is refluxed for 48 hours in 50 ml of tetrahydrofuran. The reaction mixture is evaporated down, the residue is taken up in water and extracted with ethyl acetate. The organic phase is evaporated down and the residue is saponified in a mixture of 20 ml of ethanol and 6 ml of 4N sodium hydroxide solution at 50° C. for 30 minutes. The reaction mixture is neutralised by the addition of citric acid and extracted with ethyl acetate. The organic phase is concentrated by evaporation and the residue is recrystallised from ethyl acetate/diisopropylether.

Yield: 25% of theory

Melting point: 142°-144° C.

$C_{29}H_{29}ClN_2O_3$ (467.57); Calculated: C 74.50, H 6.25, N 8.99; Found: 74.32, 6.23, 8.85.

EXAMPLE 8

6-[3-(3-(4-Chlorophenyl)-ureido)-phenyl]-6-(3-pyridyl)-hex-5-enoic acid 2.4 g of methyl 6-(3-aminophenyl)-6-(3-pyridyl)-hex-5-enoate and 1.5 g of 4-chlorophenylisocyanate are stirred in 50 ml of tetrahydrofuran at ambient temperature for one hour. The reaction mixture is evaporated down, the residue is mixed with water and extracted with ethyl acetate/ethanol (9:1). The organic phase is evaporated down and the residue is saponified in 60 ml of ethanol and 6 ml of 4N sodium hydroxide solution at 50° C. for one hour. The reaction mixture is evaporated down, the residue is taken up in 100 ml of water and extracted with ethyl acetate. The aqueous phase is neutralised by the addition of citric acid, whereupon the product is precipitated. The precipitate is suction filtered, washed with water and diisopropylether and recrystallised from ethyl acetate/diisopropylether.

Yield: 52% of theory

Melting point: 172°-173° C.

$C_{24}H_{22}ClN_2O_3$ (435.91); Calculated: C 66.13, H 5.09, N 9.64; Found: 66.04, 5.22, 9.71.

The following compounds are obtained analogously to Example 8:

6[-3-(3-(3-chlorophenyl)-ureido)-phenyl]-6-(3-pyridyl)-hex-5-enoic acid
  Melting point: 151°–152° C.
  $C_{24}H_{22}ClN_2O_3$ (435.91); Calculated: C 66.13, H 5.09, N 9.64; Found: 66.05, 5.18, 9.52.

6-[3-(3-(2,5-dimethylphenyl)-ureido)-phenyl]-6-(3-pyridyl)-hex-5-enoic acid
  Melting point: 137° C. (decomp.)
  $C_{26}H_{27}ClN_2O_3$ (429.52); Calculated: C 72.71, H 6.34, N 9.78; Found: 72.58, 6.35, 9.75.

6-[3-(3-(2-chlorophenyl)-ureido)-phenyl]-6-(3-pyridyl)-hex-5-enoic acid
  Melting point: 170°–172° C.
  $C_{24}H_{22}ClN_2O_3$ (435.91); Calculated: C 66.13, H 5.09, N 9.64; Found: 66.03, 5.22, 9.45.

6-[3-(3-(1-naphthyl)-ureido)-phenyl]-6-(3-pyridyl)-hex-5-enoic acid
  Melting point: 173° C.
  $C_{28}H_{25}ClN_2O_3$ (451.53); Calculated: C 74.48, H 5.58, N 9.31; Found: 74.32, 5.53, 9.16.

6-[3-(3-(3,4-dichlorophenyl)-ureido)-phenyl]-6-(3-pyridyl)-hex-5-enoic acid
  Melting point: 178° C.
  $C_{24}H_{21}ClN_2O_3$ (470.36); Calculated: C 61.29, H 4.5, N 8.93; Found: 61.24, 4.61, 9.10

6-[3-(3-(2,4-dichlorophenyl)-ureido)-phenyl]-6-(3-pyridyl)-hex-5-enoic acid
  Melting point: 126° C.
  $C_{24}H_{21}ClN_2O_3$ (470.36); Calculated: C 61.29, H 4.50, N 8.93; Found: 61.01, 4.69, 8.99.

6-[3-(3-(2,3-dichlorophenyl)-ureido)-phenyl]-6-(3-pyridyl)-hex-5-enoic acid
  Melting point: 196° C.
  $C_{24}H_{21}ClN_2O_3$ (470.36); Calculated: C 61.29; H 4.50; N 8.93; Found: 61.14, 4.66, 8.82.

6-[3-(3-(3-nitrophenyl)-ureido)-phenyl]-6-(3-pyridyl)-hex-5-enoic acid
  Melting point: 207°–208° C.
  $C_{24}H_{22}ClN_2O_3$ (446.47); Calculated: C 64.57; H 4.97, N 12.55; Found: 64.58, 4.97, 12.36.

6-[3-(3-(4-carboxyphenyl)-ureido)-phenyl]-6-(3-pyridyl)-hex-5-enoic acid
  Melting point: from 118° C. (decomp.)
  $C_{25}H_{23}N_2O_3$ (445.48); Calculated: C 67.41, H 5.20, N 9.43; Found: 67.27, 5.17, 9.21.

6-[3-(3-benzylureido)-phenyl]-6-(3-pyridyl)-hex-5-enoic acid
  Melting point: 166°–168° C.
  $C_{25}H_{25}N_2O_3$ (415.49); Calculated: C 72.27; H 6.06, N 10.11; Found: 72.10, 6.07, 9.91.

6-[3-(3-(4-tert.butylphenyl)-ureido)-phenyl]-6-(3-pyridyl)-hex-5-enoic acid
  Melting point: 180°–182° C.
  $C_{28}H_{31}N_2O_3$ (457.57); Calculated: C 73.50, H 6.83, N 9.18; Found: 73.38, 6.78, 9.20.

6-[3-(3-benzoylureido)-phenyl]-6-(3-pyridyl)-hex-5-enoic acid
  Melting point 190°–191° C.
  $C_{25}H_{23}ClN_2O_3$ (429.48); Calculated: C 69.92, H 5.40, N 9.78; Found: 69.72, 5.34, 9.58.

6-[3-(3-(4-methylbenzenesulphonyl)-ureido)-phenyl]-6-(3-pyridyl)-hex-5-enoic acid
  Melting point: 183° C. (decomp.)
  $C_{25}H_{25}N_2O_3$ (479.56); Calculated: C 62.62, H 5.25, N 8.76; Found: 62.80, 5.41, 8.68.

6-[3-(3-cyclohexylureido)-phenyl]-6-(3-pyridyl)-hex-5-enoic acid
  Melting point: 163°–164° C.
  $C_{24}H_{29}N_2O_3$ (407.51); Calculated: C 70.74, H 7.17, N 10.3; Found: 70.66, 7.36, 10.38.

6-[3-(3-(tert.butyl)-ureido)-phenyl]-6-(3-pyridyl)-hex-5-enoic acid
  Reaction in a mixture of tetrahydrofuran, dimethylformamide and 4-dimethylaminopyridine with heating.
  Melting point: 165° C.
  $C_{22}H_{27}N_2O_3$ (381.48); Calculated: C 69.27, H 7.13, N 11.02; Found: 69.24, 7.05, 10.91.

6-[3-(3-(2,4-dichlorophenyl)-1-methylureido)-phenyl]-6-(3-pyridyl)-hex-5-enoic acid
  Melting point: 139°–141° C.
  $C_{25}H_{23}Cl_2N_2O_3$ (484.38); Calculated: C 61.99, H 4.79, N 8.68; Found: 61.86, 4.91, 8.58.

6-[3-(3-(4-carboxyphenyl)-1-methylureido)-phenyl]-6-(3-pyridyl)-hex-5-enoic acid
  Purification by column chromatography on silica gel using methylene chloride/ethanol (30:1)
  Foam, $R_f$ value: 0.52 (silica gel; methylene chloride/ethanol = 20:1)
  $C_{26}H_{25}N_2O_3$ (459.50); Calculated: C 67.96, H 5.48, N 9.14; Found: 67.88, 5.56, 8.96.

6-[4-(3-(3-chlorophenyl)-ureido)-phenyl]-6-(3-pyridyl)-hex-5-enoic acid
  Melting point: 175°–176° C.
  $C_{24}H_{22}ClN_3O_3$ (435.91); Calculated: C 66.13, H 5.09, N 9.64; Found: 65.99, 5.14, 9.58.

6-[4-(3-(2,4-dichlorophenyl)-1-methylureido)-phenyl]-6-(3-pyridyl)-hex-5-enoic acid
  Melting point: 150°–152° C.
  $C_{25}H_{23}Cl_2N_3O_3$ (484.38); Calculated: C 61.99, H 4.79, N 8.67; Found: 61.88, 4.78, 8.49.

6-[4-(3-(4-methylbenzenesulphonyl)-ureido)-phenyl]-6-(3-pyridyl)-hex-5-enoic acid
  Melting point: 176° C. (decomp.)
  $C_{25}H_{25}N_2O_3$ (479.55); Calculated: C 62.62, H 5.25, N 8.76; Found: 62.59, 5.38, 8.48.

5-[3-(3-(3-chlorophenyl)-ureido)-phenyl]-5-(3-pyridyl)-pent-4-enoic acid
  Purification by column chromatography on silica gel with methylene chloride/ethanol (9:1)
  Foam, $R_f$ value: 0.25 (silica gel; methylene chloride/ethanol = 19:1)
  $C_{23}H_{20}ClN_3O_3$ (421.88) Calculated: C 65.48, H 4.78, N 9.96; Found: 65.23, 4.87, 9.66.

7-[3-(3-(3-chlorophenyl)-ureido)-phenyl]-7-(3-pyridyl)-hept-6-enoic acid
  Melting point: 140°–141° C.
  $C_{25}H_{24}ClN_3O_3$ (449.94); Calculated: C 66.74, H 5.38, N 9.34; Found: 66.63, 5.34, 9.25.

EXAMPLE 9

6-[4-(3,3-Diphenylureido)-phenyl]-6-(3-pyridyl)-hex-5-enoic acid

A mixture of 2.4 g of methyl 6-(4-aminophenyl)-6-(3-pyridyl)-hex-5-enoate and 2.1 g of N,N-diphenyl-carbamoylchloride is stirred in 25 ml of pyridine for 18 hours at ambient temperature. The solvent is eliminated and the residue is taken up in ethyl acetate. The organic phase is washed with water, dried and evaporated down. The residue is saponified in a mixture of 20 ml of ethanol and 6 ml of 4N sodium hydroxide solution for 30 minutes at 50° C. The reaction solution is diluted with water and extracted with ethyl acetate. Then the aqueous phase is neutralised by the addition of citric acid, the precipitate formed is suction filtered and recrystallised from ethyl acetate/isopropanol.

Yield: 55% of theory

Melting point: 155°–156° C.

$C_{30}H_{27}N_3O_3$ (477.56); Calculated: C 75.45; H 5.70, N 8.80; Found: 75.28, 5.89, 8.68.

The following compounds are obtained analogously to Example 9

6-[4-(3-methyl-3-phenylureido)-phenyl]-6-(3-pyridyl)-hex-5-enoic acid

Melting point: 118°–120° C.

$C_{25}H_{25}N_3O_3$ (415.29); Calculated: C 72.27, H 6.07, N 10.11; Found: 72.19, 6.16, 10.00.

6-[4-(1,3-dimethyl-3-phenylureido)-phenyl]-6-(3-pyridyl)-hex-5-enoic acid

Resin, $R_f$ value: 0.60 (silica gel; methylene chloride/ethanol=20:1)

$C_{26}H_{27}N_3O_3$ (429.52); Calculated: C 72.71, H 6.34, N 9.78; Found: 72.55, 6.44, 9.54.

6-[3-(1,3-dimethyl-3-phenylureido)-phenyl]-6-(3-pyridyl)-hex-5-enoic acid Resin, $R_f$ value: 0.40 (silica gel; methylene chloride/ethanol=20:1)

$C_{26}H_{27}N_3O_3$ (429.52) ; Calculated: C 72.71, H 6.34, N 9.78; Found: 72.53, 6.34, 9.59.

EXAMPLE 10

6-[3-(3-(4-Chlorophenyl)-thioureido)-phenyl]-6-(3-pyridyl)-hex-5-enoic acid 2.4 g of methyl 6-(3-aminophenyl)-6-(3-pyridyl)-hex-5-enoate and 1.7 g of 4-chlorophenylisothiocyanate are stirred in 30 ml of tetrahydrofuran for 1.5 hours at ambient temperature. The solvent is eliminated, the residue is taken up in water and extracted with ethyl acetate. The organic phase is evaporated down and the residue is saponified in a mixture of 20 ml of ethanol and 6 ml of 4N sodium hydroxide solution at ambient temperature for 90 minutes. The reaction mixture is diluted with water, extracted with ethyl acetate and then neutralised by the addition of citric acid. The aqueous phase is extracted with ethyl acetate. The organic phase is evaporated down and the residue is purified over a silica gel column using methylene chloride/ethanol (20:1).

Yield: 64% of theory

Foam, $R_f$ value: 0.31 (silica gel; methylene chloride/acetone=2:1).

$C_{24}H_{22}ClN_3O_2$ (451.98); Calculated: C 63.78, H 4.91, N 9.30; Found: 63.62, 5.03, 9.11.

The following compounds are obtained analogously to Example 10:

6-[3-(3-(3-chlorophenyl)-thioureido)-phenyl]-6-(3-pyridyl)-hex-5-enoic acid

Melting point: 142°–144° C. (ethyl acetate/tert.-butylmethylether)

$C_{24}H_{22}ClN_3O_2S$ (451.98); Calculated: C 63.78, H 4.91, N 9.30; Found: 63.69, 5.11, 9.10.

6-[3-(3-(2-chlorophenyl)-thioureido)-phenyl]-6-(3-pyridyl)-hex-5-enoic acid

Melting point: 146°–148° C. (isopropanol/diisopropylether)

$C_{24}H_{22}ClN_3O_2S$ (451.98); Calculated: C 63.78, H 4.91, N 9.30; Found: 63.87, 5.06, 9.10.

6-[3-(3-(2,4-dichlorophenyl)-thioureido)-phenyl]-6-(3-pyridyl)-hex-5-enoic acid

Melting point: 154°–155° C. (ethyl acetate/diisopropylether)

$C_{24}H_{21}Cl_2N_3O_2S$ (486.41); Calculated: C 59.26, H 4.35, N 8.64; Found: 59.18, 4.53, 8.37.

6-[3-(3-(4-methylphenyl)-thioureido)-phenyl]-6-(3-pyridyl)-hex-5-enoic acid

Melting point: 137° C. (ethyl acetate/tert.butylmethyl-ether)

$C_{25}H_{25}N_3O_2S$ (431.56); Calculated: C 69.58, H 5.84, N 9.74; Found: 69.38, 5.92, 9.59.

6-[3-(3-(4-nitrophenyl)-thioureido)-phenyl]-6-(3-pyridyl)-hex-5-enoic acid

Melting point: 139° C. (isopropanol/dioxane)

$C_{24}H_{22}N_4O_4S$ (462.53); Calculated: C 62.23, H 4.7, N 12.11; Found: 62.08, 4.88, 12.00.

6-[3-(3-(tert.butyl)-thioureido)-phenyl]-6-(3-pyridyl)-hex-5-enoic acid

Reaction in a mixture of tetrahydrofuran, dimethylformamide and 4-dimethylaminopyridine with heating.

Melting point: 137°–139° C.

$C_{22}H_{27}N_3O_2S$ (397.54); Calculated: C 66 47, H 6.85, N 10.57; Found: 66.49, 6.95, 10.48.

6-[3-(3-(2,4-dichlorophenyl)-1-methylthioureido)-phenyl]-6-(3-pyridyl)-hex-5-enoic acid Melting point: 124°–26° C. (ethyl acetate/diisopropyl-ether)

$C_{25}H_{23}Cl_2N_3O_2S$ (500.44); Calculated: C 60.00, H 4.63, N 8.40; Found: 59.95, 4.82, 8.25.

6-[4-(3-(2,4-dichlorophenyl)-1-methylthioureido)-phenyl]-6-(3-pyridyl)-hex-5-enoic acid Melting point: 127°–129° C. (ethyl acetate/petroleum ether)

$C_{25}H_{23}Cl_2N_3O_2S$ (500.44); Calculated: C 60.00, H 4.6, N 8.40; Found: 59.8, 4.50, 8.56.

EXAMPLE 11

6-[3-(N-Methyl-2-hydroxy-2-phenylacetylamino)-phenyl]-6-(3-pyridyl)-hex-5-enoic acid 4.66 g of methyl 6-(3-methylaminophenyl)-6-(3-pyridyl)-hex-5-enoate, 3.2 g of DL-0-acetylmandelic acid chloride and 3.5 ml of triethylamine are stirred in 50 ml of methylene chloride at ambient temperature for one hour. The reaction mixture is washed with water and evaporated down. The residue is saponified in a mixture of 30 ml of ethanol and 10 ml of 4N sodium hydroxide solution at 50° C. for 30 minutes. The reaction mixture is neutralised by the addition of citric acid and extracted with ethyl acetate. The organic phase is washed with water, evaporated down and the residue is purified over a silica gel column using ethyl acetate.

Yield: 69% of theory

Foam, $R_f$ value: 0.38 (silica gel; methylene chloride/acetone=20:1)

$C_{26}H_{26}N_2O_4$ (430.50); Calculated: C 72.54; H 6.09, N 6.51; Found: 72.34, 6.09, 6.52.

EXAMPLE 12

Methyl 6-[4-(4-methylbenzenesulphonylamino)-phenyl]-6-(3-pyridyl)-hex-5-enoate 3 g of methyl 6-(4-aminophenyl)-6-(3-pyridyl)-hex-5-enoate, 1.9 g of tosylchloride and 5 ml of triethylamine are stirred in 100 ml of methylene chloride at ambient temperature for one hour. The reaction mixture is washed with water, dried and evaporated down. Ther esidue is purified over a silica gel column with ethyl acetate.

Yield: 78% of theory

Oil, $R_f$ value: 0.74 (silica gel; ethyl acetate)

$C_{24}H_{26}N_2O_4S$ (450.56); Calculated: C 66.65, H 5.82, N 6.22; Found: 66.53, 5.89, 6.08.

EXAMPLE 13

Tablets containing 100 mg of (−)-5E-6-]4-(Z-2-(4-chlorophenyl)-cyclopropyl-1-carboxamido)-phenyl]-6-(3-pyridyl)-hex-5-enoic acid

| Composition: | |
|---|---|
| 1 tablet contains: | |
| Active substance | 100.0 mg |
| Lactose | 80.0 mg |
| Corn starch | 34.0 mg |
| Polyvinylpyrrolidone | 4.0 mg |
| Magnesium stearate | 2.0 mg |
| | 220.0 mg |

PREPARATION PROCESS

The active substance, lactose and starch are mixed together and uniformly moistened with an aqueous solution of the polyvinylpyrrolidone. After the moist masses have been screened (2.0 mm mesh size) and dried in a rack dryer at 50° C. they are screened again (1.5 mm mesh) and the lubricant is added. The mixture produced is formed into tablets.

| Weight of tablet: | 220 mg |
|---|---|
| Diameter: | 9 mm, biplanar, facetted on both sides and notched on one side. |

EXAMPLE 14

Hard gelatin capsules containing 150 mg of (−)-5E-6-[4-(Z-2-(4-chlorophenyl)-cyclopropyl-1-carboxamido)-phenyl]-6-(3-pyridyl)-hex-5-enoic acid

| 1 capsule contains: | |
|---|---|
| Active substance | 150.0 mg |
| Dried corn starch about | 180.0 mg |
| Powdered lactose about | 87.0 mg |
| Magnesium stearate | 3.0 mg |
| about | 320.0 mg |

PREPARATION

The active substance is mixed with the excipients, passed through a 0.75 mm mesh screen and homogeneously mixed in a suitable apparatus.

The final mixture is packed into size 1 hard gelatin capsules.

Capsule contents: about 320 mg
Capsule shell: size 1 hard gelatin capsule.

EXAMPLE 15

Suppositories containing 150 mg of (-)-5E-6-[4-(Z-2-(4-chlorophenyl)-cyclopropyl-1-carboxamido)-phenyl]-6-(3-pyridyl)-hex-5-enoic acid

| 1 suppository contains: | |
|---|---|
| Active substance | 150.0 mg |
| Polyethyleneglycol (M.W. 1500) | 550.0 mg |
| Polyethyleneglycol (M.W. 6000) | 460.0 mg |
| Polyethylene sorbitan monostearate | 840.0 mg |
| | 2000.0 mg |

PREPARATION

After the suppository masses have been melted the active substance is homogeneously distributed therein and the melt is poured into chilled moulds.

EXAMPLE 16

Suspensions containing 50 mg of (−)-5E-6-[4-(Z-2-(4-chlorophenyl)-cyclopropyl-1-carboxamido)-phenyl]-6-(3-pyridyl)-hex-5-enoic acid

| 100 ml of suspension contain: | | |
|---|---|---|
| Active substance | | 1.0 g |
| Sodium salt of carboxymethylcellulose | | 0.2 g |
| Methyl p-hydroxybenzoate | | 0.05 g |
| Propyl p-hydroxybenzoate | | 0.01 g |
| Glycerol | | 5.0 g |
| 70% Sorbitol solution | | 50.0 g |
| Flavouring | | 0.3 g |
| Distilled water | ad | 100 ml |

PREPARATION

Distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the addition of the sorbitol solution and flavouring, the suspension is evacuated to eliminate air, with stirring.

5 ml of suspension contain 50 mg of active substance.

EXAMPLE 17

Tablets containing 150 mg of (-)-5E-6-[4-(Z-2-(4-chlorophenyl)-cyclopropyl-1-carboxamido)-phenyl]-6-(3-pyridyl)-hex-5-enoic acid

| Composition: | |
|---|---|
| 1 tablet contains: | |
| Active substance | 150.0 mg |
| Powdered lactose | 89.0 mg |
| Corn starch | 40.0 mg |
| Colloidal silica | 10.0 mg |
| Polyvinylpyrrolidone | 10.0 mg |
| Magnesium stearate | 1.0 mg |
| | 300.0 mg |

PREPARATION

The active substance mixed with lactose, corn starch and silica is moistened with a 20% aqueous polyvinylpyrrolidone solution and passed through a 1.5 mm mesh screen. The granules dried at 45° C. are rubbed through the same screen again and mixed with the specified amount of magnesium stearate. Tablets are compressed from the mixture.

| Weight of tablet: | 300 mg |
|---|---|
| Punch | 10 mm, flat |

EXAMPLE 18

Film-coated tablets containing 75 mg of
(−)-5E-6-[4-(Z-2-(4-chlorophenyl)-cyclopropyl-1-carboxamido)-phenyl]-6-(3-pyridyl)-hex-5-enoic acid

| 1 tablet core contains: | |
|---|---|
| Active substance | 75.0 mg |
| Calcium phosphate | 93.0 mg |
| Corn starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

PREPARATION

The active substance is mixed with calcium phosphate, corn starch, polyvinylpyrrolidone, hydroxypropylmethylcellulose and half the specified amount of magnesium stearate. Using a tablet making machine, compressed tablets are produced about 13 mm in diameter which are then rubbed through a 1.5 mm mesh screen on a suitable machine and mixed with the remaining magnesium stearate. These granules are compressed in a tablet making machine to form tablets of the desired shape.

| Weight of core: | 230 mg |
|---|---|
| Punch: | 9 mm, convex |

The tablet cores thus produced are coated with a film consisting essentially of hydroxypropylmethyl-cellulose. The finished film coated tablets are glazed with beeswax.

Weight of film coated tablet: 245 mg

Obviously all the other compounds of general formula I may be used as active substances in the galenic preparations described above.

EXAMPLE 19

Film-coated tablets containing 75 mg of
(−)-5E-6-[4-(Z-2-(4-chlorophenyl)-cyclopropyl-1-carboxamido)-phenyl]-6-(3-pyridyl)-hex-5-enoic acid (Substance B) +75 mg of PDE-inhibitor

| A powdered mixture of | |
|---|---|
| Dipyridamole | 25% |
| Substance B | 25% |
| Fumaric acid | 15% |
| Cellulose | 20% |
| Corn starch | 8% |
| Polyvinylpyrrolidone | 6% | is moistened with water in a mixing vessel and granulated through a screen with a mesh size of 1.5 mm. After drying and rescreening, 1% magnesium stearate is added and 10 mm biconvex tablets weighing 300 mg are produced. These tablets are sprayed with hydroxypropyl-methylcellulose lacquer until they weight 312 mg.

EXAMPLE 20

Hard gelatin capsules, containing 200 mg of
(−)-5E-6-[4-(Z-2-(4-chlorophenyl)-cyclopropyl-1-carboxamido)-phenyl]-6-(3-pyridyl)-hex-5-enoic acid (Substance B)+50 mg of PDE-inhibitor 10 kg of dipyridamole, 20 kg of fumaric acid, 11.5 kg of polyvinylpyrrolidone, 40 kg of substance B, 1.5 kg of silicon dioxide and 0.8 kg of magnesium stearate are mixed for 15 minutes in a cube mixer. This mixture is fed through a roller compactor behind which is a dry granulating apparatus with screening means. The fractions measuring 0.25 to 1.0 mm are used. The capsule filling machine is set so that each size 0 capsule contains a quantity of granules corresponding to 50 mg of PDE-inhibitor and 200 mg of substance B.

EXAMPLE 21

Hard gelatin capsules containing 100 mg of
(−)-5E-6-[4-(Z-2-(4-chlorophenyl)-cyclopropyl-1-carboxamido)-phenyl]-6-(3-pyridyl)-hex-5-enoic acid (Substance B) +250 mg of PDE-inhibitor a) Granules 125 kg of mopidamole, 50 kg of fumaric acid and 13.5 kg of lactose are mixed together and moistened with a solution of water/polyethyleneglycol 6000. After granulation through a screen with a mesh size of 1.0 mm and drying at 45° C., 1.4 kg of stearic acid are added.

b) Coated tablets 100 kg of substance B, 7.5 kg of hydroxypropylmethyl-cellulose, 2.5 kg of silicon dioxide and 15 kg of carboxymethylcellulose are moistened with ethanol and granulated through a screen with a mesh size of 1.5 mm. After drying, I kg of magnesium stearate are added and the granules are compressed to form biconvex tablets weighing 126 mg with a diameter of 5.5 mm.

These cores are coated in several steps with a coating suspension consisting of 5.6 kg of saccharose, 0.5 kg of gum arabic and 3.8 kg of talc until the tablets weigh 135 mg.

c) Packaging

The quantity of granules corresponding to 250 mg of PDE-inhibitor are packed into a size 0 long hard gelatin capsule in a special capsule filling machine and the coated tablet containing 100 mg of substance B is placed on top.

EXAMPLE 22

Suspension containing 10 mg of
(−)-5E-6-[4-(Z-2-(4-chlorophenyl)-cyclopropyl-1-carboxamido)-phenyl]-6-(3-pyridyl)-hex-5-enoic acid (Substance B)+100 mg of dipyridamole per 5 g The suspension has the following composition:

| (1) | Dipyridamole | 2.0% |
|---|---|---|
| (2) | Substance B | 0.2% |
| (3) | Sorbitol | 20.8% |
| (4) | Cellulose | 7.5% |
| (5) | Sodium carboxymethylcellulose | 2.5% |
| (6) | Flavour correctors/preservatives | 1.8% |
| (7) | Water | 65.2% |

Ingredients (3)-(6) are stirred into hot water under high shear forces. After cooling, (1), (2) and (7) are incorporated in the viscous suspension.

EXAMPLE 23

Delayed release preparation containing 50 mg of (—)-5E-6-[4-(Z-2(4-chlorophenyl)-cyclopropyl-1-carboxamido)-phenyl]-6-(3-pyridyl)-hex-5-enoic acid (Substance B) +200 mg of dipyridamole a) Pellet I

| A mixture of | |
|---|---|
| Substance B | 50.0 kg |
| Lysine | 12.5 kg |
| High polymeric hydroxypropylcellulose | 52.5 kg |
| Triacetine | 4.0 kg |
| Ethyl cellulose | 2.5 kg |
| Magnesium stearate | 3.5 kg | is kneaded with ethanol in a special extruder and extruded in the form of spaghetti (1 mm in diameter) which is rounded off into pellets in a spheronizer. These pellets are then dried thoroughly.

b) Pellet II 300 kg of mixed tartaric acid starter pellets are sprayed in a special container with a suspension consisting of isopropanol, dipyridamole and polyvinyl-pyrrolidone until the pellets of active substance thus produced contain about 45% dipyridamole.

These pellets are sprayed with a lacquer consisting of methacrylic acid/methylmethacrylate copolymer (brand name Eudragit S) and hydroxypropylmethylcellulose-phthalate (brand name HP 55) in a weight ratio of 85:15 to 50:50. The organic lacquer solutions also contain plasticiser and talc. Two pellet components are sprayed with 5 and 7% coating agents and different proportions of the lacquer components within the limits specified. The two components are mixed together so as to give the following in vitro release:

Conditions (corresponding to USPXXI, Basket Method, 100 rpm, 1st hour: artificial gastric juice, pH 1.2, 2nd to 6th hours: artificial intestinal juice (phosphate buffer), pH 5.5):

Release of active substance per hour:

| 1st hour | about 30% |
|---|---|
| 2nd hour | about 25% |
| 3rd hour | about 18% |
| 4th hour | about 12% | after the 6th hour more than 90% of the dipyridamole has been released.

c) Packaging

The pellets are mixed together in accordance with the active substance content of pellet components I and II and the desired dosage, and are packed into size 0 long capsules in a capsule filling machine.

EXAMPLE 24

Ampoules containing 5 mg of (—)-5E-6-[4-(Z-2-(4-chlorophenyl)-cyclopropyl-1-carboxamido)-phenyl]-6-(3-pyridyl)-hex-5-enoic acid (Substance B)+10 mg of dipyridamole per 5 ml

| Composition: | | |
|---|---|---|
| (1) | Dipyridamole | 10 mg |
| (2) | Substance B | 5 mg |
| (3) | Propyleneglycol | 50 mg |
| (4) | Polyethyleneglycol | 5 mg |
| (5) | Ethanol | 10 mg |
| (6) | Water for injections ad | 5 ml |
| (7) | 1N HCl ad | pH 3 |

The active substances are dissolved with heating in a solution consisting of ingredients (3) - (7). After the pH has been checked and the mixture filtered sterile, it is poured into suitable ampoules and sterilised.

What is claimed is:

1. A pyridyl derivative of the formula

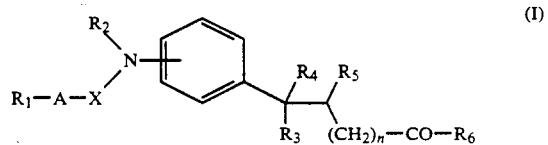

wherein n represents the number 2, 3 or 4,

X represents a carbonyl or thiocarbonyl group, $R_1$ represents an optionally phenyl-substituted $C_{1-4}$-alkyl group or a $C_{5-7}$-cycloalkyl group, or $R_1$ represents a phenyl group or, if A does not represent a bond, $R_1$ may represent a benzoyl or benzenesulphonyl group in which each phenyl moiety may be mono-, di- or trisubstituted by fluorine, chlorine or bromine atoms or by $C_{1-4}$-alkoxy or $C_{1-4}$-alkyl groups which substituents may be identical or different and one of the substituents may also represent a trifluoromethyl, carboxyl, amino or nitro group, or $R_1$ may also represent a naphthyl, biphenylyl, diphenylmethyl, indolyl, thienyl, chlorothienyl or bromothienyl group, $R_2$ represents a hydrogen atom or a $C_{1-4}$-alkyl group, $R_3$ represents a 2-, 3-, 4-pyridyl group, $R_4$ and $R_5$ each represent a hydrogen atom or together represent another carbon-carbon bond, $R_6$ represents a hydroxy or $C_{1-3}$-alkoxy group, and A represents a bond, a $C_{3-4}$-cycloalkylene or $C_{3-4}$-cycloalkylidene group wherein a methylene group may be replaced by a dichloromethylene group, or A represents a straight-chained, optionally mono- or polyunsaturated $C_{2-3}$-alkylene group, an —$R_7CR_8$, —O—$R_7CR_8$—, —O—$CH_2CH_2$—, —O—$CH_2CH_2CH_2$— or —$NR_9$— group, wherein $R_7$ represents a hydrogen atom, a hydroxy, phenyl or $C_{1-3}$-alkyl group, $R_8$ represents a hydrogen atom or a $C_{1-3}$-alkyl group and $R_9$ represents a hydrogen atom, a $C_{1-3}$-alkyl group or a phenyl group, the enantiomers thereof, the cis- or trans-isomers thereof if $R_4$ and $R_3$ together represent a carbon-carbon bond, or an addition sal thereof.

2. A pyridyl derivative as recited in claim 1, wherein n represents the number 2, 3 or 4, X represents a carbonyl or thiocarbonyl group, $R_1$ represents a phenyl group or, if A does not represent a bond, $R_1$ may also represent a benzoyl or benzenesulphonyl group in which each phenyl moiety may be monosubstituted by a fluorine, chlorine or bromine atom, by a trifluoromethyl, phenyl, methoxy, carboxy or nitro group or by a $C_{1-4}$-alkyl group, or $R_1$ may represent a phenyl group or, if A does not represent a bond, $R_1$ may also represent a benzoyl or benzenesulphonyl group in which each phenyl moiety is disubstituted by chlorine or bromine atoms or by methyl groups which substituents may be identical or different, or $R_1$ may represent a cyclohexyl, benzyl, 4-amino-3,5-dichlorophenyl, 4-amino-3,5-dibromophenyl, naphthyl, diphenylmethyl, indolyl, thienyl, chlorothienyl or bromothienyl group, $R_2$ represents a hydrogen atom or a $C_{1-3}$-alkyl group, $R_3$ represents a 3-pyridyl group, $R_4$ and $R_5$ each represent a hydrogen atom or together represent another carbon-carbon bond, $R_6$ represents a hydroxy or $C_{1-3}$-alkoxy group and A represents a bond, a cyclopropylene or cyclopropylidene group wherein a methylene group may be replaced by a dichloromethylene group, a straight-chained, optionally mono- or polyunsaturated alkylene group having 2 carbon atoms, or an $—R_7CR_8—$, $—O—R_7CR_8—$ or $—NR_9—$ group, wherein $R_7$ represents a hydrogen atom, a hydroxy or a $C_{1-2}$-alkyl group, $R_8$ represents a hydrogen atom or a $C_{1-2}$-alkyl group and $R_9$ represents a hydrogen atom, an alkyl group having 1 or 2 to 3 carbon atoms or a phenyl group, the enantiomers thereof, the cis- or trans-isomers thereof if $R_4$ and $R_5$ together represent a carbon-carbon bond, or an addition salt thereof.

3. A pyridyl derivative as recited in claim 1, wherein n represents the number 2, 3 or 4, X represents a carbonyl or thiocarbonyl group, $R_1$ represents a phenyl group optionally monosubstituted by a fluorine, chlorine or bromine atom, by a trifluoromethyl, phenyl, methoxy, carboxy or nitro group or by a $C_{1-4}$-alkyl group, or $R_1$ represents a phenyl group disubstituted by chlorine or bromine atoms or methyl groups these substituents being either identical or different, or $R_1$ represents a benzyl, 4-amino-3,5-dichlorophenyl, naphthyl or chlorothienyl group, $R_2$ represents a hydrogen atom or a methyl group, $R_3$ represents a 3-pyridyl group, $R_4$ and $R_5$ each represent a hydrogen atom or together represent another carbon-carbon bond, $R_6$ represents a hydroxy group and A represents a bond, a cyclopropylene or cyclopropylidene group, a straight-chained, optionally mono- or polyunsaturated $C_2$-alkylene group, an $—R_7CR_8—$, $—O—R_7CR_8—$ or $—NR_9—$ group, wherein $R_7$ represents a hydrogen atom or a hydroxy or methyl group, $R_8$ represents a hydrogen atom or a methyl group and $R_9$ represents a hydrogen atom or a methyl or phenyl group, the enantiomers thereof, the cis- or trans-isomers thereof if $R_4$ and $R_5$ together form a carbon-carbon bond, or an addition salt thereof.

4. A pyridyl derivative as recited in claim 1, wherein the pyridyl derivative is selected from the group consisting of:

(−)-5E-6-[4-(Z-2-(4-chlorophenyl)-cyclopropyl-1-carboxamido)phenyl]-6-(3-pyridyl)-hex-5-enoic acid, 5E-6-[3-(3-(4-chlorophenyl)-propionylamino)-phenyl]-6-(3-pyridyl)-hex-5-enoic acid, 5E-6-[3-(3-(4-chlorophenyl)-thioureido)-phenyl]-6-(3-pyridyl)-hex-5-enoic acid, E-6-[3-(3-(2,4-dichlorophenyl)-1-methylthioureido)-phenyl]-6-(3-pyridyl)-hex-5-enoic acid, the cis- and trans-isomers thereof, and an addition salt thereof.

5. (−)-5E-6-[4-(Z-2-(4-chlorophenyl)-cyclopropyl-1-carboxamido)-phenyl]-6-(3-pyridyl)-hex-5-enoic acid, the cis- or trans-isomers thereof, or the addition salts thereof.

6. A pharmaceutical composition comprising a pyridyl derivative as recited in claim 1 and one or more inert carriers or diluents.

7. A pharmaceutical composition comprising a pyridyl derivative as recited in claim 2 and one or more inert carriers or diluents.

8. A pharmaceutical composition comprising a pyridyl derivative as recited in claim 3 and one or more inert carriers or diluents.

9. A pharmaceutical composition comprising a pyridyl derivative as recited in claim 4 and one or more inert carriers or diluents.

10. A pharmaceutical composition comprising a pyridyl derivative as recited in claim 5 and one or more inert carriers or diluents.

11. A method for the treatment of thromboembolic disorders in a patient which comprises administering to the patient a therapeutically effective amount of the pyridyl derivative as recited in claim 1.

12. A method for the treatment of arteriosclerosis in a patient which comprises administering to the patient a therapeutically effective amount of the pyridyl derivative as recited in claim 1.

13. A method for the treatment of ischaemia, asthma or allergies, in a patient which comprises administering to the patient a therapeutically effective amount of the pyridyl derivative as recited in claim 1.

14. A method for the treatment of diseases in a patient in which a thromboxane-mediated constriction or $PGE_2$-mediated dilation of the patient's capillaries is involved, which comprises administering to the patient a therapeutically or prophylactically effective amount of the pyridyl derivative as recited in claim 1.

15. A method for alleviating the severity of organ transplant rejection in a patient, which comprises administering to the patient an effective amount of the pyridyl derivative as recited in claim 1.

16. A method for reducing the renal toxicity of immunesuppressant drugs in a patient, which comprises administrating to the patient an effective amount of the pyridyl derivative as recited in claim 1.

17. A method for treating kidney disease in a patient, which comprises administering to the patient a therapeutically effective amount of the pyridyl derivative as recited in claim 1.

18. A method for treating shock in a patient, which comprises administering to the patient a therapeutically effective amount of the pyridyl derivative as recited in claim 1.

* * * * *